United States Patent [19]
Szoka, Jr. et al.

[11] Patent Number: 6,113,946
[45] Date of Patent: *Sep. 5, 2000

[54] SELF-ASSEMBLING POLYNUCLEOTIDE DELIVERY SYSTEM COMPRISING DENDRIMER POLYCATIONS

[75] Inventors: Francis C. Szoka, Jr., San Francisco, Calif.; Jean Haensler, Petite Rosselle, France

[73] Assignee: The Regents of the University of California, Oakland, Calif.

[*] Notice: This patent is subject to a terminal disclaimer.

[21] Appl. No.: 08/469,433

[22] Filed: Jun. 6, 1995

Related U.S. Application Data

[63] Continuation of application No. 08/092,200, Jul. 14, 1993, abandoned, which is a continuation-in-part of application No. 07/913,669, Jul. 14, 1992, abandoned, which is a continuation-in-part of application No. 07/864,876, Apr. 3, 1992, abandoned.

[51] Int. Cl.[7] .......................... A61K 9/14; A61K 31/70; C07H 21/00; C07H 21/04
[52] U.S. Cl. .......................... 424/486; 514/44; 536/23.1
[58] Field of Search .......................... 435/172.3, 6, 7.1, 435/91.1, 91.3, 172.1, 375, 320.1, 455, 468, 471; 424/450, 400, 486; 514/2, 12, 44; 530/300, 324; 536/23.1, 24.5

[56] References Cited

U.S. PATENT DOCUMENTS 4,946,787  8/1990  Epstein et al. .......................... 435/240.2

OTHER PUBLICATIONS

Parente et al. Mechanism of leakage of phospholipid vesicle contents induced by peptide GALA. Biochem. 29: 8720–8728, 1990.
Subbarao et al. pH–dependent bilayer desabilization by an ampipathic peptide. Biochem. 26: 2964–2972, 1987.
Gura "Antisense has growing pains" Science 270: 575–577, Oct. 1995.
Crystal "Transfer of genes to humans: Early lessons and obstacles to success" Science 270: 404–410, Oct. 1995.
Stull et al. "Antigene, ribozyme, and aptamer nucelic acid drugs: Progress and prospects" Pharmacetical Res. 12 (4): 465–483, Apr. 1995.
"Report and recommendations of the panel to assess the NIH investment in research on gene therapy" Orkin and Motulsky co–chairs. National Institutes of Health, Dec. 1995.
Riordan, J.R., et al., Science 245:1066 (1989).
Karem, B., et al., Science 245:1073 (1989).
Friedman, T., Science 244:1275 (1989).
Bluestone, M., Botechnol. 10:132 (1992).
Rosenfeld, M.A., et al., Cell 68:143 (1992).
Rosenfeld, M.A., et al., Science 252:431 (1991).
Felgner, P.L., et al., Nature 349:351 (1991).
Capecchi, M.R., Cell 22:479 (1980).
Nicolau, C., et al., Crit. Rev. Ther. Drugg Carr. Sys. 6:239 (1989).
Mannio, R.J, et al., Biotechniques 6:682 (1988).
Lu, L., et al., Pflugers Arch. 415:198 (1989).
Hazinski, T.A., et al., Am. J. Espir. Cell Mol. Biol. 4:206 (1991).
Brigham, K.L., et al., Am. J. Med. Sci. 298:278 (1989).
Loeffler, J., et al., J. Neurochem. 54:1812 (1990).
Zhou, X., et al., Biochim. Biophys .Acta 1065:8 (1991).
Gao, X., et al., Biochim. Biophys. Res. Comm. 179:280 (1991).
Düzgünes, N., et al., Biochem. 28:9179 (1989).
Lai, M.Z., et al, Biochem. 24:1646 (1985).
Wu, G.Y., et al., J. Biol. Chem. 262:4429 (1987).
Wu, G.Y., et al., J. Biol. Chem. 263:14621 (1988).
Huckett, et al., Biochem. Pharmacol., 40:253 (1990).
Wagner, et al., P.N.A.S. (USA) 87:3410 (1990).
Curiel, D.T., e t al., P.N.A.S. (USA), 88:8850 (1991).
Behr, J.P., Tet. Lett. 27:5861 (1986).
Dingwall, C., et al., TIBS 16:478 (1991).
Kaneda, Y., et al., Science 243:375 (1989).
Silver, P.A., Cell 64:489 (1991).
Finlay, D.R., et al., J. Cell Sci. Supp. 11:225 (1989).
Tikchonenko, T.I., et al., Gene 63:321 (1988).
Böttger, M., et al., Biochim. Biophys. Acta 950:221 (1988).
Nielsen, P.E., Eur. J. Biochem. 122:283 (1982).
Ellens et al., Biochem. 25:285 (1986).
Tomalia et al. (1990), Angew. Chem. Int. Ed. Engl. 29: 138–175.

*Primary Examiner*—John S. Brusca
*Assistant Examiner*—Thomas G. Larson
*Attorney, Agent, or Firm*—Nathan P. Koenig; Crosby, Heafey, Roach & May

[57] ABSTRACT

A self-assembling polynucleotide delivery system comprises a dendrimer polycation aiding in the delivery of the polynucleotide to a desired address, and optionally other agents such as DNA masking agents, cell recognition agents, charge-neutralization agents, membrane-permeabilization agents, and subcellular-localization agents.

64 Claims, 8 Drawing Sheets

FIG._1

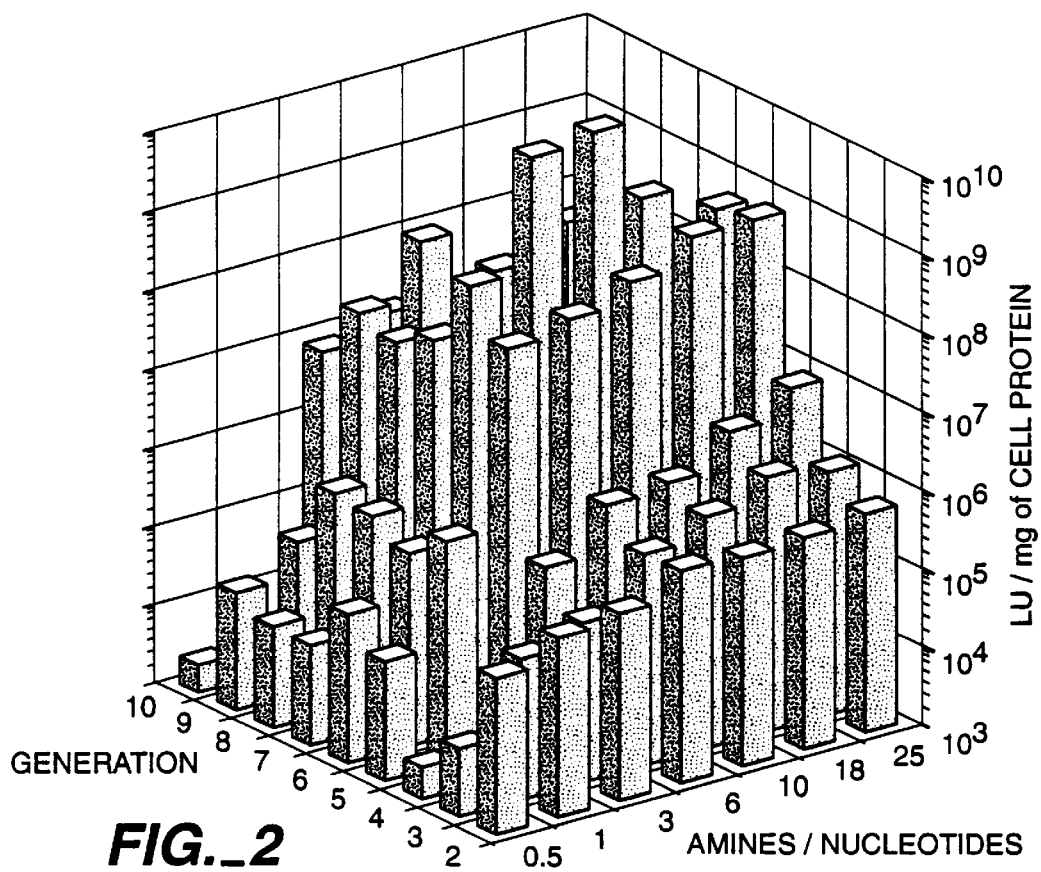
FIG._2
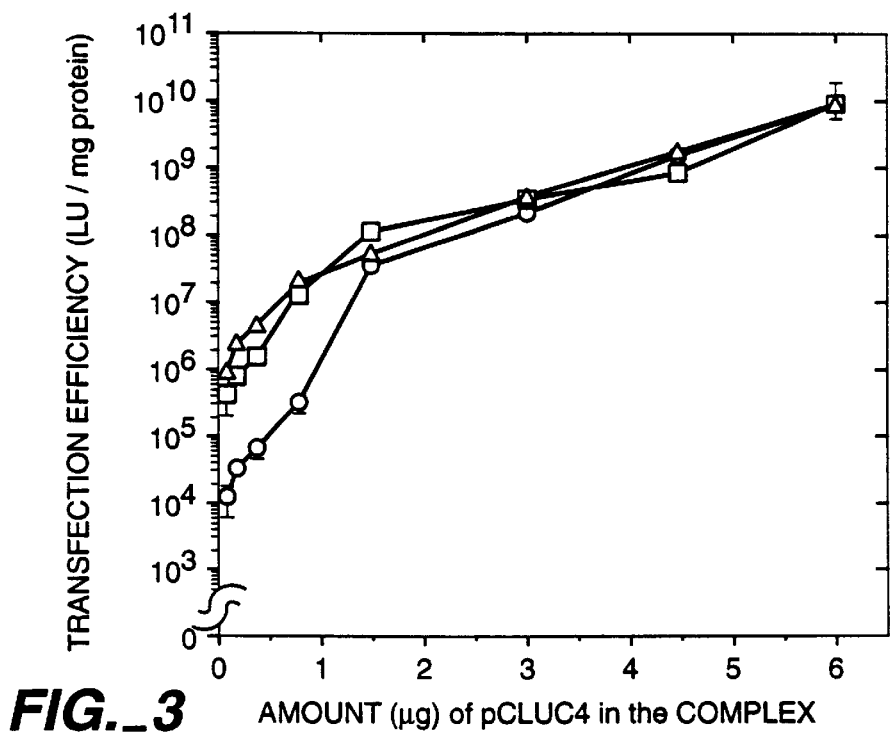
FIG._3

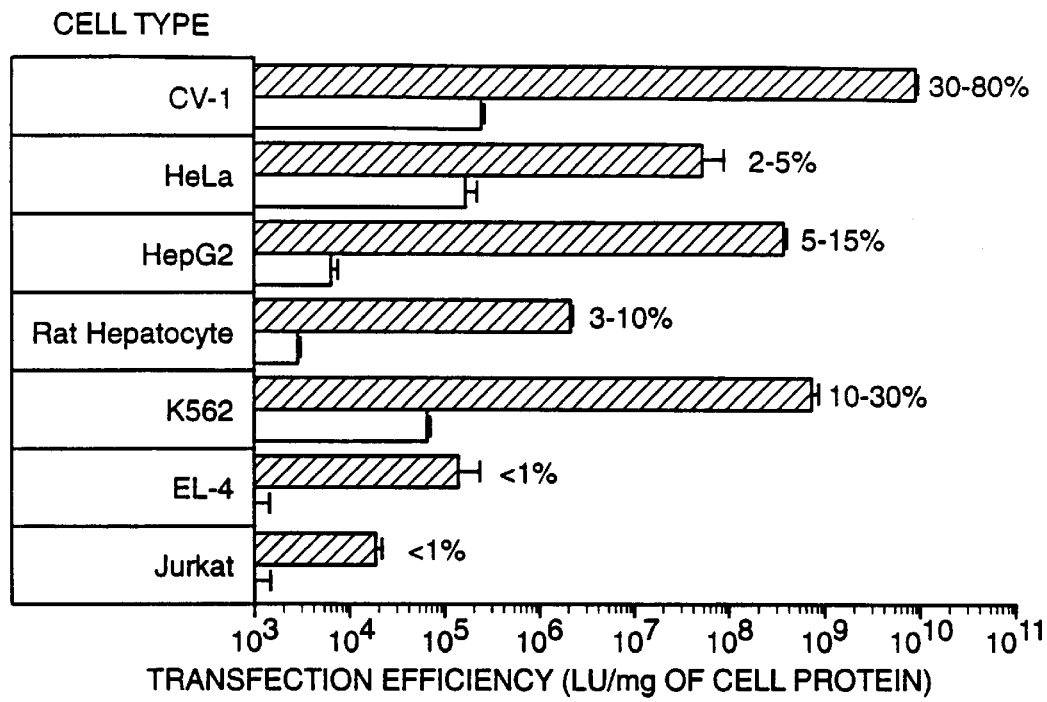
FIG._4A
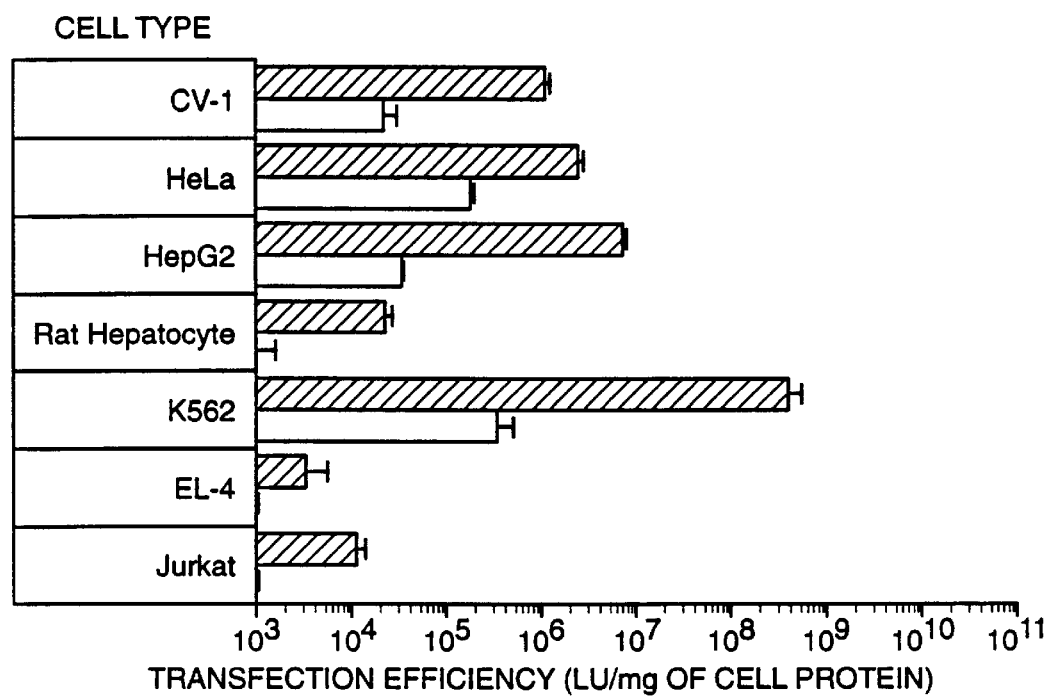
FIG._4B

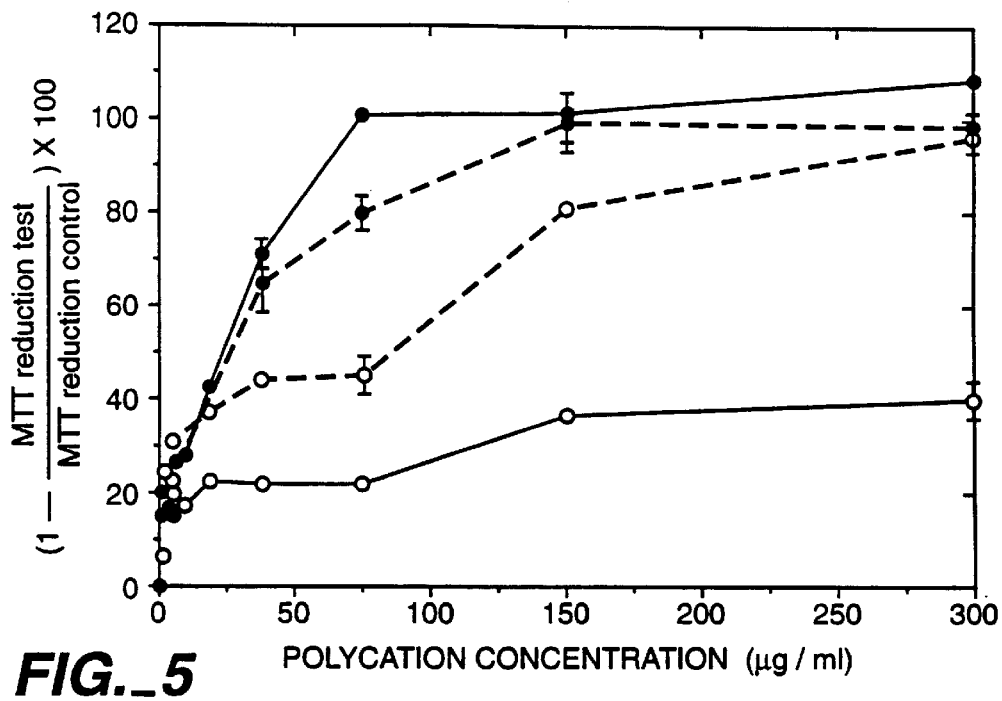
FIG._5
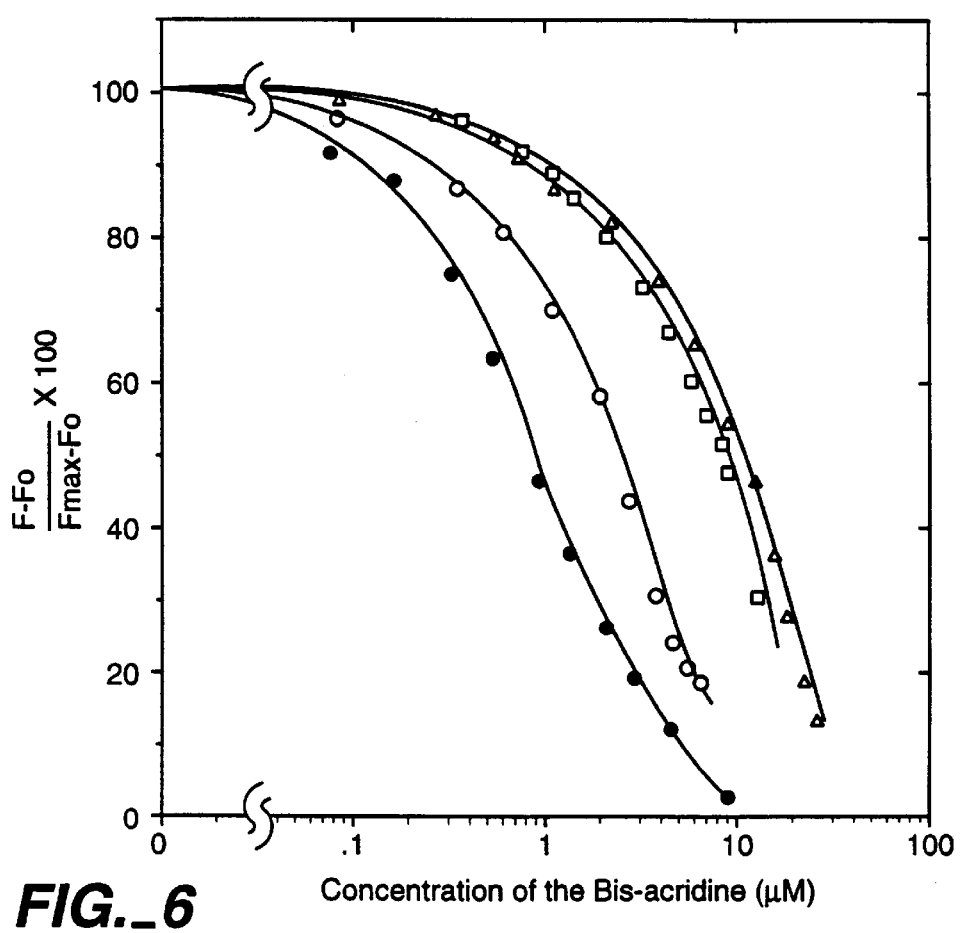
FIG._6

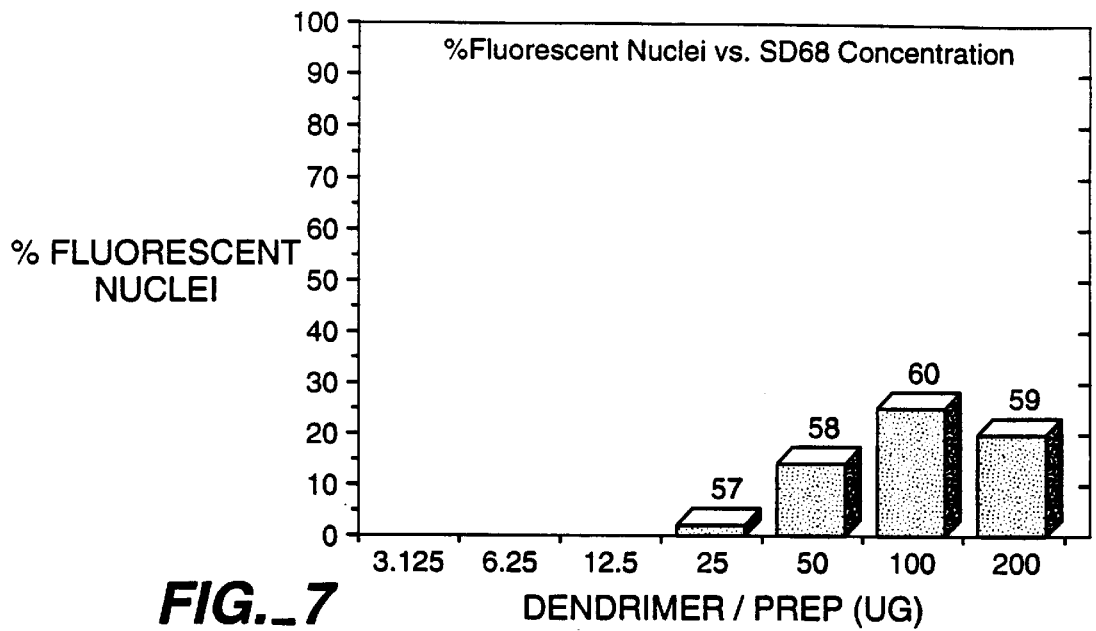
FIG._7
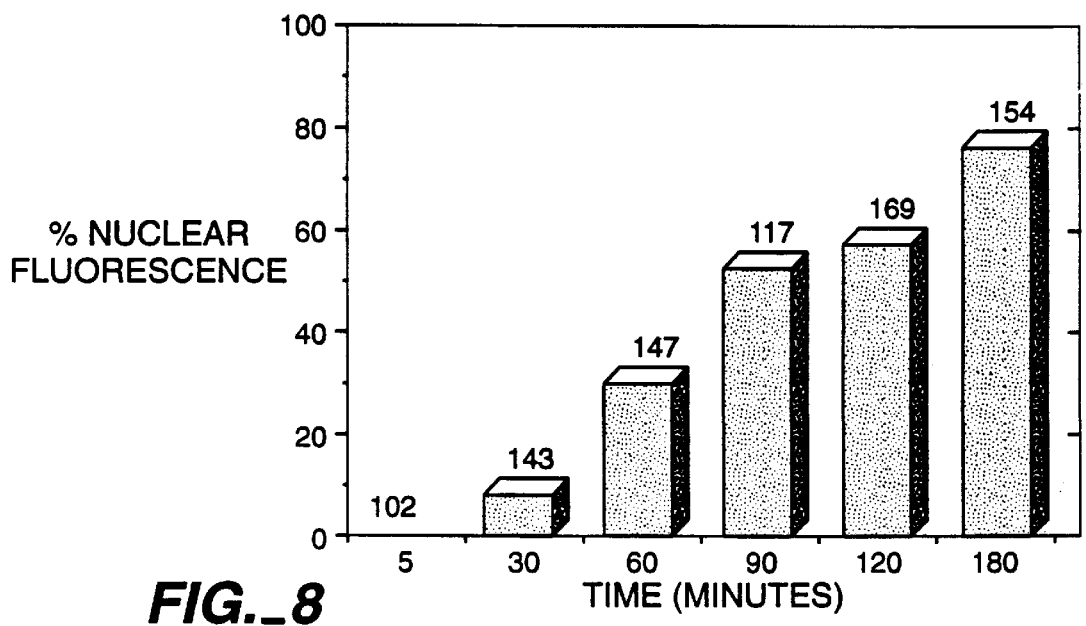
FIG._8

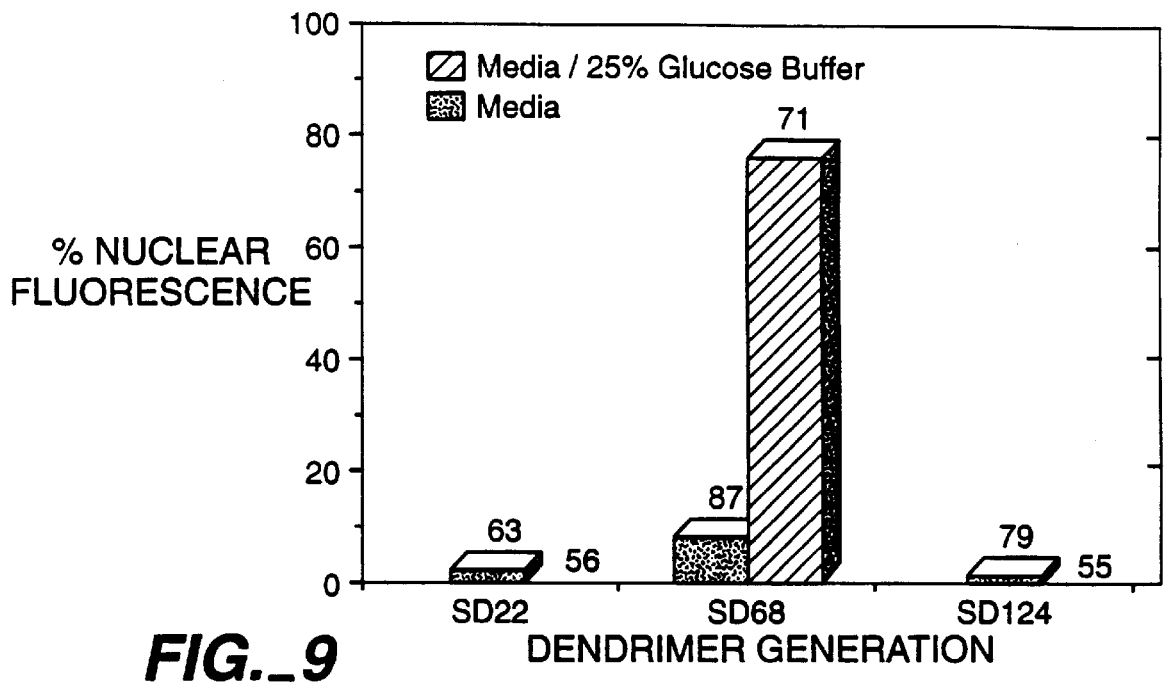
FIG._9
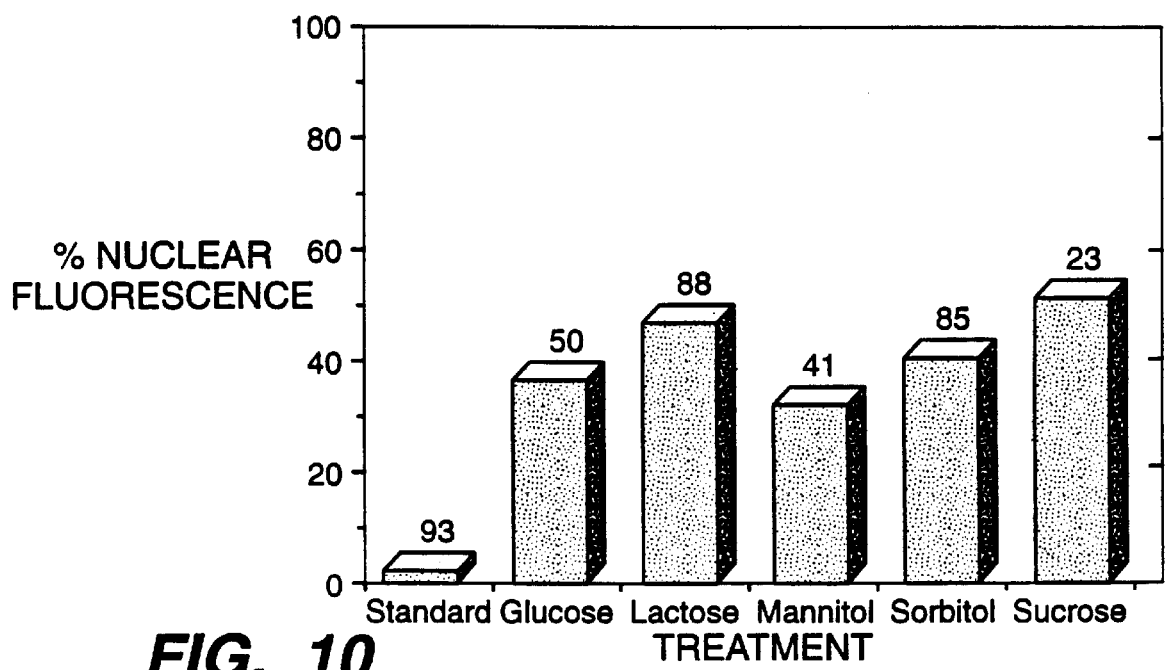
FIG._10

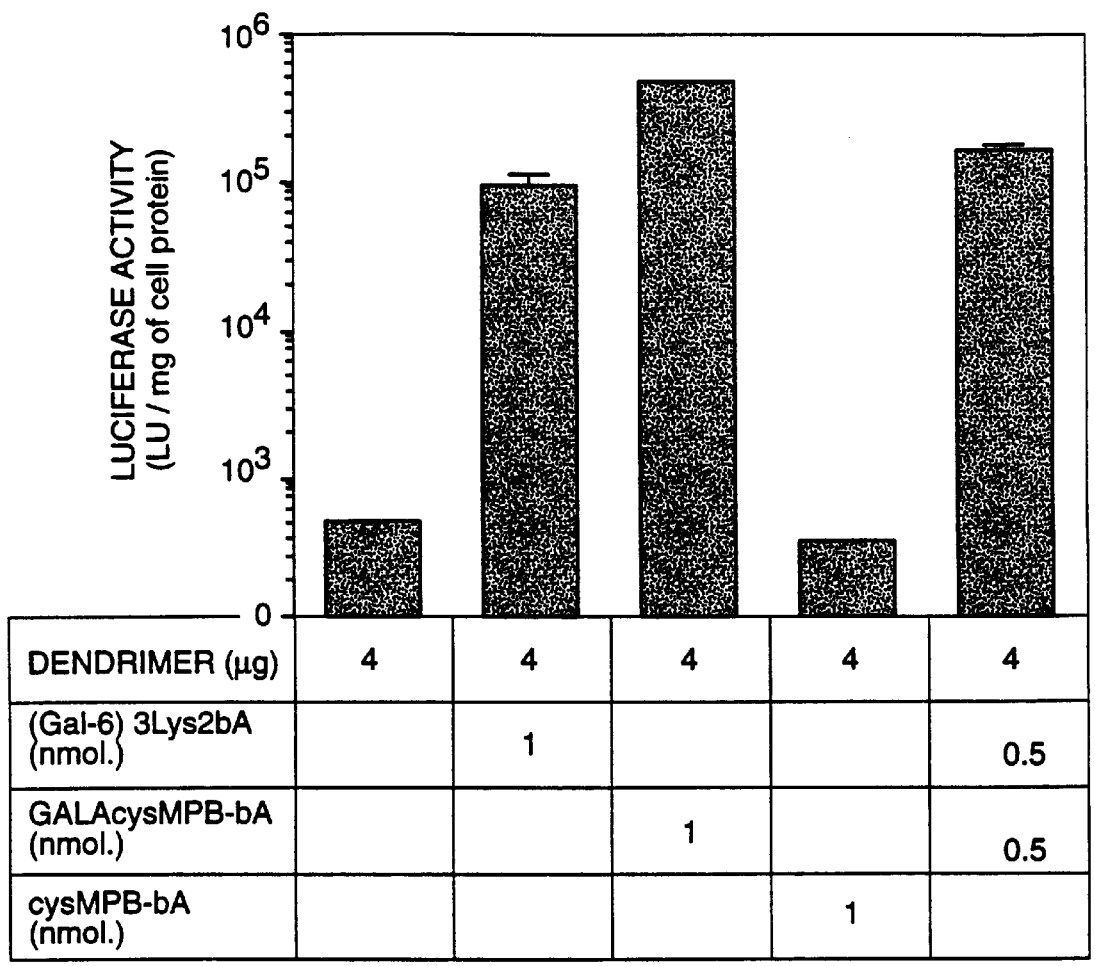
FIG._11

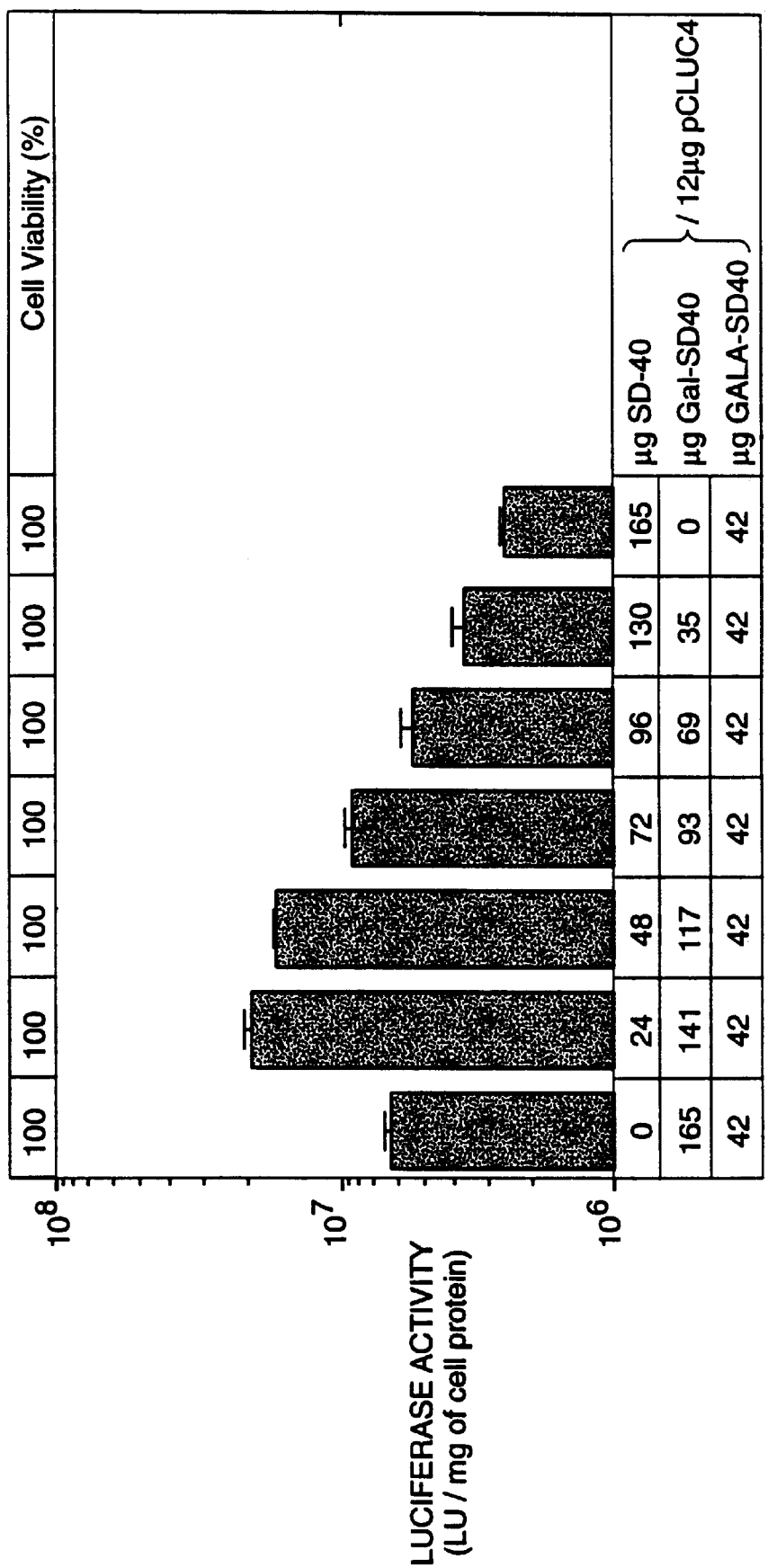
FIG._12

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:1:

Pro Lys Lys Lys Arg Lys Val
    1              5

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear

```
        (ix) FEATURE:
            (A) NAME/KEY: Modified-site
            (B) LOCATION: 1
            (D) OTHER INFORMATION: /note= "This position is
                N-formyl-."

(xi) SEQUENCE DESCRIPTION: SEQ ID NO:2:

Xaa Met Leu Phe
    1

(2) INFORMATION FOR SEQ ID NO:3:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:3:

Cys Ser Gly Arg Glu Asp Val Trp
    1               5

(2) INFORMATION FOR SEQ ID NO:4:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:4:

Ala Ala Phe Glu Asp Leu Arg Val Leu Ser
    1               5                   10

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:5:

Lys Arg Pro Arg Pro
    1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:6:

Lys Phe Glu Arg Gln
    1               5

(2) INFORMATION FOR SEQ ID NO:7:

(i) SEQUENCE CHARACTERISTICS:
            (A) LENGTH: 16 amino acids
            (B) TYPE: amino acid
            (C) STRANDEDNESS: single
            (D) TOPOLOGY: linear (xi) SEQUENCE DESCRIPTION: SEQ ID NO:7:
```

-continued

```
Met Leu Ser Leu Arg Gln Ser Ile Arg Phe Phe Lys Pro Ala Thr Arg
1               5                   10                  15
```

(2) INFORMATION FOR SEQ ID NO:8:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:8:

```
Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Cys Ala Ala
16              20                  25                  30
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:9:

```
Cys Gly Tyr Gly Pro Lys Lys Lys Arg Lys Val Gly Gly
1               5                   10
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:10:

```
Cys Gly Tyr Gly Pro Lys Asp Lys Arg Lys Val Gly Gly
1               5                   10
```

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:11:

```
Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala
16              20                  25                  30
```

SELF-ASSEMBLING POLYNUCLEOTIDE DELIVERY SYSTEM COMPRISING DENDRIMER POLYCATIONS

This is a continuation of application Ser. No. 08/092,200, filed on Jul. 14, 1993, now abandoned, which is a continuation-in-part of U.S. application Ser. No. 07/913,669 filed Jul. 14, 1992, now abandoned, which is a continuation-in-part of U.S. application Ser. No. 07/864,876, filed Apr. 3, 1992, now abandoned.

ACKNOWLEDGMENT OF GOVERNMENT SUPPORT

The government has rights in this invention pursuant to Grant No. GM-30163 awarded by the National Institutes of Health.

BACKGROUND OF THE INVENTION

1. Field of the Invention

This invention relates to the field of oligonucleotide delivery systems and gene therapy. In particular, this invention is directed to a self-assembling polynucleotide delivery system comprising a polynucleotide and a dendrimer polycation, and optionally other agents, aiding the delivery of the polynucleotide to a desired subcellular-location. The polynucleotide and the other agents are in general associated with the polynucleotide via non-covalent interactions. Agents suitable for use herein include DNA-masking components, cell recognition agents, charge-neutralization agents, membrane-permeabilization agents, and subcellular localization agents, among others.

2. Description of the Background

Molecular biologists have identified the chromosomal defects in a large number of human hereditary diseases, raising the prospects for cures using gene therapy. This emerging branch of medicine aims to correct genetic defects by transferring cloned and functionally active genes into the afflicted cells. Cystic fibrosis (CF) is a fatal recessive genetic disease characterized by abnormalities in chloride transport. The locus of the disease has been traced to mutations in the gene encoding the cystic fibrosis transmembrane conductance regulator (CFTR). Correction of the underlying gene defect by complementation or replacement of the defective CFTR is the ultimate cure for CF.

Gene therapy or the in vivo delivery and expression of genes is a fast-developing science that can be used to replace defective genes. Several systems and polymers suitable for the delivery of polynucleotides are known in the art. Among them, viral vectors such as adenoviral vectors have been used to transfer CFTR to the cotton rat lung in vivo. Although high levels of in vivo transfection have been reported with the adenoviral vectors, non-viral delivery systems have a number of advantages for the delivering of polynucleotides.

During the past decade, a number of methods have been developed to introduce functional genes into mammalian cells in vitro. These techniques are applicable to gene therapy, provided that the target cells can be removed from the body, transfected, and the transfected cells amplified and then returned to the patient. This, however, is not possible for CF patients.

At present, the best invivo transfection efficiencies are obtained with retroviruses. However, the efficiency of transfection is variable and virus based gene delivery systems have the risk of causing viral infection or cancer. Clearly, although no acute complications have been observed stemming from the use of retroviral vectors in humans, the possibility of long-term complications mandate careful patient monitoring.

The potential risks of using viral based vectors and the conceptual advantages of using instead plasmid DNA constructs for gene therapy have led to the development of various physical and chemical methods for aiding gene transfer in the absence of viral vectors. The most intensely studied systems involve the treatment of cells with calcium phosphate or a cationic facilitator. Other methods involve the injection of the DNA during physical puncturing of the membrane or passive uptake of the DNA during permeabilization or abrasion of the cellular membrane. Each of the these methods is intrinsically aggressive and is not preferred for in vivo use.

The use of a direct gene delivery system that does not involve the use of viral vehicles may avoid the risks posed by viral systems. A non-viral carrier suitable for gene delivery must be able to surmount many barriers. It must survive in the circulation and be able to target the cell of choice, to introduce DNA into the cytoplasm of the cell, and to transport the DNA into the nucleus.

At present, viruses are the most efficient vectors for gene transfer, but the potential risks associated with their use have catalyzed a search for synthetic DNA-delivery systems. Early work showed that polycations such as polylysine and DEAE-dextran promote the uptake of proteins and single- and double-stranded polynucleotides into animal cells, and since then, polylysine-based vectors have been extensively tested for gene transfer. However, these polycations are relatively cytotoxic and by themselves not very efficient, which limits their usefulness for transfecting cells in culture.

In spite of these drawbacks, polylysines have a number of advantages such as helping to
1) assemble DNA into a compact structure,
2) destabilize cell membranes, and
3) provide a handle for the attachment of other effectors to the nucleic acid.

The neutralization and condensation of DNA by polylysines into small (ca 100 nm) toroid-like structures, promotes the endocytosis of the nucleic acid into cells in vitro. The endocytic process may be further stimulated by the covalent attachment to the polycation of specific ligands like transferrin, asialoorosomucoid or insulin. When polycation transfection procedures are based upon receptor-mediated or fluid phase endocytosis, a large fraction of the endocytosed DNA becomes trapped in intracellular vesicles and is ultimately degraded in the lysosomes. Lysosomal degradation can be partially bypassed by the addition of lysosomotrophic agents such as chloroquine during transfection, or by attachment of endosome disrupting agents, such as inactivated viruses or viral fusogenic peptides to the polylysine. The ability of polylysine-DNA complexes to transfect cells is strongly dependent upon the presence of these effectors.

One form of protecting the polynucleotide in the circulation, so that it survives long enough to arrive at the desired cellular destination, is the "masking" or protecting of the polynucleotide.

Microparticulates, such as erythrocyte ghosts, reconstituted viral envelopes and liposomes have been used in part as protection in gene transfer. A successful liposome system uses the cationic lipid N-[1(-2,3-dioleoyloxy)propyl]-N,N, N-trimethylammonium chloride (DOTMA), mixed with phosphatidylethanolamine (PE) to form the reagent Lipofectin™. Lipofectin™ is a cationic liposome which may be mixed with the DNA, and the mixture added to a cell without need for encapsulation of the DNA inside the liposome with cationic reagents. Lipofectin™ has been used to transfect reporter genes into human lung epithelial cells in culture, to introduce the chloramphenicol acetyltransferase (CAT) gene into rat cells by the intratracheal route, and to introduce the CAT gene into mice cells by the intratracheal and intravenous routes. In the case of the CAT gene, about 50% of the airway epithelial rat cells transiently expressed the β-galactosidase reporter gene, although the level of expression was not quantitated. When the CAT gene was attached to a steroid sensitive promoter and transfected into rat lung, its expression was shown to be positively regulated by dexamethasone. Cytotoxicity, however, is a definite problem when high concentrations of Lipofectin™ are used.

Substitutes for DOTMA including lipopolyamine, lipophilic polylysines, and a cationic cholesterol have been used to mediate gene transfer in culture. Although some of these show an about three fold improvement over the transfection rates observed with Lipofectin™, their toxicity remains a problem. The mechanism responsible for transfection using cationic lipids has not been thoroughly explored. The past approach has been to synthesize different cationic lipids and try them in transfection assays, rather than to systematically study how the delivery systems introduce DNA into a cell. The finding that DOTMA/PE liposomes can undergo bilayer fusion with anionic liposomes suggests that DOTMA may facilitate the direct entry of the DNA via the plasma membrane. On the other hand, for high efficiency transfection cationic lipids systems require PE, possibly because PE can form intramembrane lipid intermediates which facilitate membrane fusion.

Efficient gene transfer also requires the targeting of the DNA to the cell of choice. Various procedures based upon receptor mediated endocytosis have recently been described for gene transfer. A cell-specific ligand-polylysine conjugate was bound to nucleic acids through charge interactions, and the resulting complex was taken up efficiently by the target cells, such as in the case of the human hepatoma cell line HepG2 and of rat hepatocytes in vivo using this delivery system with asialoorosomucoid as a ligand. The stable expression of an enzymatic activity in HepG2 cells following insulin-directed targeting as well as the transferrin-polycation-mediated delivery of a plasmid into the human leukemic cell line K-562 and the subsequent expression of the encoded luciferase gene, have been reported. However, the described delivery systems require the linking of high molecular weight targeting proteins to DNA through a polylysine linker. These large ligand-polycation conjugates are heterogenous in size and composition, chemically ill-defined, and difficult to prepare in a reproducible fashion. Moreover, in many of the receptor mediated systems, chloroquine or other disruptors of intracellular trafficking are required for high levels of transfection. In one study, an adenovirus was used to enhance gene delivery of a receptor mediated system.

Thus, genes can be delivered into the interior of mammalian cells by receptor mediated endocytosis, with a fraction of the exogenous DNA escaping degradation, entering the nucleus, and being expressed. The level of expression, however, is low, probably due to the limited entry of the foreign DNA into the cytoplasm.

The direct delivery of genes is also aided by neutralization of the large negative charge on the polynucleotide, and the (often concomitant) ability to permeabilize the membrane of the targeted cell. The use of polycations to neutralize the polynucleotide charge aids the permeabilization of the membrane and the translocation of the polynucleotide. Cationic lipids have also been used for this purpose. Certain cationic lipids termed lipopolyamines and lipointercalants are also known.

Once the polynucleotide has entered the targeted cell, the direct delivery of genes may be aided by directing the genes to the proper subcellular location. One obvious target for the delivery of deoxyribonucleotides is the nucleus. Ligands known to aid in this process are nuclear localization peptides or proteins containing nuclear localization sequences.

The transfection efficiency obtained with reconstituted viral envelopes was shown to increase when the foreign gene is co-delivered into the target cells with nuclear proteins. DNA mixed with nuclear proteins was shown to exhibit a modest increase in transfection over DNA mixed with albumin used as control. Thus, the DNA appears to be incorporated into the nucleus more readily when proteins containing the nuclear localization sequence (NLS) pro-lys-lys-lys-arg-lys-val SEQ ID NO:1 is associated with the plasmid since the presence of the NLS on a protein designates it for transport through the nuclear pore. Nuclear localization sequences of 14 amino acids have been attached to a variety of macromolecules and even to gold particles (150 Å diameter) and, when introduced into the cytoplasm, they were rapidly incorporated into the nucleus. Nuclear entry appears to be the rate limiting step for successful, stable transfection. This is supported by the finding that when plasmid DNA is microinjected into the cytoplasm, it is unable to bring about cell transfection. No transfection occurred out of 1000 cytoplasmic injections, whereas the microinjection of plasmids directly into the nucleus results in transfection in greater than 50% of the microinjected cells.

The transfection efficiency was also shown to increase when the DNA is condensed using various cationic proteins. Although the reason why DNA condensation increases transfection is not readily apparent, it may be due to an increase in the cellular uptake of DNA or to a decrease in the susceptibility of the DNA to nucleases, which may result in higher amounts of intact DNA in the cell.

The direct delivery of genes associated with one of the above-discussed classes of agents, is further aided by the ability of those agents to remain associated with the DNA. Examples of this are the association of a receptor ligand with a polynucleotide by covalent attachment of the ligand to the polycation polylysine, and optionally by covalently attaching the ligand to a DNA intercalator, e.g., ethidium homodimer (5,5'-diazadecamethylenebis(3,8-diamino-6-phenylphenanthridium) dichloride dihydrochloride) and the association of photoaffinity labels to DNA by covalent attachment to 9-aminoacridine and certain bis-acridines.

Dendrimers are bulky three-dimensional polymers built by reiterative reaction sequences around a core molecule that may be prepared in varied molecular weights and sizes (Tomalia, D. A., et al., "Starburst Cascade Polymers: Molecular-Level Control of Size, Shape, Surface Chemistry, Topology, and Flexibility from Atoms to Macroscopic Matter", Agnew. Chem. Int. Ed. Engl. 29:138 (1990)).

However, in the quest for attaining better results in the field of gene therapy, there is still a need for improved polynucleotide delivery systems of high transfection efficiency without the drawbacks of prior systems.

SUMMARY OF THE INVENTION

This invention relates to a self-assembling polynucleotide delivery system utilizing a dendrimer polycation, preferably non-covalently coupled to a polynucleotide to be delivered, and optionally one or more, preferably two or more of the following agents.

1) DNA-masking agents.
2) Cell recognition agents.
3) Charge-neutralization and membrane-permeabilization agents.
4) Subcellular localization agents.

The dendrimer polycation is capable by itself of delivering the polynucleotide with high transfection efficiency. Each optional component in this system is able to perform its indicated function and is also capable of assembling or disassembling with the polynucleotide as required. For example, a certain component may have to dissociate itself from the polynucleotide in order to perform its desired function.

This invention provides a composition for delivering a polynucleotide to a subcellular component of a eukaryotic cell comprising a polynucleotide and a dendrimer polycation operatively linked thereto.

In one embodiment of the present composition, the polynucleotide comprises a hybrid vector having a structural gene operatively coupled thereto.

The composition of the invention may be contacted with a target eukaryotic cell under conditions effective to attain highly efficient transfection.

In another aspect, the invention also encompasses the administration of the present composition to an organism to deliver to specifically target cells a polynucleotide such as a structural gene under conditions of highly efficient transfection and inducing the expression in the cells of the gene product.

A more complete appreciation of the invention and many of the attendant advantages thereof will be readily perceived as the same becomes better understood by reference to the following figures.

BRIEF DESCRIPTION OF THE DRAWINGS

FIG. 1 shows the effect of PLys115, SD68, SD54 and GALA/SEQ ID NO:11-SD54 on the electrophoretic mobility of plasmid DNA. Polycation-pCMV-β-Gal complexes were prepared with each of the above and run as follows in the gel. Lane 1:pCMV-βGal alone; lane 2:2 μg of pLys115; lane 3:4 μg of pLys115; lane 4:4 μg of SD68; lane 5:6 μg of SD68; lane 6:4 μg of SD54 provided by the GALA/SEQ ID NO:11-SD54 conjugate; lane 7:160 μg of SD54 provided by the GALA/SEQ ID NO:11-SD54 conjugate; and lane 8:4 μg of SD54 provided by an equimolar mixture of SD54 and GALA/SEQ ID NO:11-SD54.

FIG. 2 shows the effect of dendrimer diameter and amount in mediating transfection in CV-1 cells (data obtained from Table 2).

FIG. 3 shows the dose-response of luciferase activity as a function of the amount of pCLuc4 plasmid used for the transfection.

FIGS. 4A and 4B show the PAMAM cascade polymer-mediated transfection of mammalian cells. FIG. 4A: Cells were transfected in duplicates with 6 μg of plasmid complexed to SD68. The transfection efficiency of the optimized complex (25 μg of SD68/6 μg of plasmid; ⊠) was compared to that obtained with complexes formed with 4 μg of SD68/6 μg of plasmid ([terminal amines]=[nucleotides]; □). Luciferase activity in the pCLuc4-transfected cells was measured 48 hrs. post transfection as described in Table 2 or 24 hrs. post transfection in the case of primary hepatocytes. Each value is the mean ± range of duplicate determinations. The percentage of transfected cells in the optimized conditions was estimated with the pCMV-βGal plasmid. Transfected cells were detected by histochemical staining using X-Gal, 24 hrs. post transfection (Lim, K. and Chae, C-B, "A Simple Assay for DNA Transfection by Incubation of the Cells in Culture Dishes with Substrate for β-Glactosydase", Biotech. 7:576 (1989)). Results are shown as percentages on the histogram. FIG. 4B: Cells were transfected as above with 6 μg of pCLuc4 complexed to 4 μg of dendrimer provided by unmodified SD54 (□) or by an equimolar mixture of unmodified SD54 and GALA/SEQ ID NO:11-SD54 (⊠).

FIG. 5 shows a comparison of the toxicity of pLys115 and SD68 on CV-1 cells. CV-1 cells in a 96 well plate were treated for 5 hrs. in serum-free DME H-21 with increasing amounts of polycation (pLys115, ● or SD68 ○) complexed ( - - - ) or not (–) to plasmid DNA and cultured for an additional 48 hrs. period in DME H-21 containing 10% FCS. After this period, toxicity of the treatments was estimated by the MTT dye recuction assay. Formazan was quantified after lysis of the cells by its absorbance at 570 nm. Background absorbance was obtained by running the assay on cells treated with 6M guanidinium hydrochloride. % reduction in cell viability={1-[$OD_{570}$(treated cells-background]/ [$OD_{570}$(untreated cells-background]}×100. Each value is the mean ± SD of triplicate determinations.

FIG. 6 shows a plot indicating the competitive displacement of ethidium bromide from calf thymus DNA by the bisacridine derivatives of Example 20. (●): Spermidine-bis-acridine trihydrochloride, Kd=4.3×$10^8$M; (○): WTcysMPB-bA, Kd=21×$10^{-7}$M; (□): cTcysMPB-bA, Kd=7.9×$10^{-7}$M; (Δ): MPB-bA, Kd =1.0×$10^{-8}$M.

FIG. 7 shows the dose-dependent effect of the SD68 dendrimer polycation on the delivery of oligonucleotides to the cell nucleus.

FIG. 8 shows the time-dependence with which the SD68 dendrimer polycation facilitates the accumulation of oligonucleotides in the nucleus of a cell (25% glucose buffer substitution).

FIG. 9 shows the effect of the generation of the dendrimer polycation on the nuclear uptake of Fitc-labeled 16meroligonucleotide.

FIG. 10 shows the nuclear fluorescence observed as a function of the dilution of the delivery composition with carbohydrate solutions.

FIG. 11 shows the effect on transfection of the attachment of a targeting ligand and membrane destabilizer to the DNA via bisacridine.

FIG. 12 shows the effect on transfection of the attachment of a targeting ligand and membrane destabilizer to the dendrimer polycation.

FIG. 13 shows one embodiment of the polynucleotide system.

Other objects, advantages and features of the present invention will become apparent to those skilled in the art from the following discussion.

DESCRIPTION OF THE PREFERRED EMBODIMENTS

Glossary

"Polynucleotide" as used herein includes RNA or DNA sequences of more than one nucleotide in either single chain, duplex or multiple chain form. The polynucleotide encompasses polydeoxyribonucleotides containing 2'-deoxy-D-ribose or modified forms thereof, i.e., DNA, polyribonucleotides containing D-ribose or modified forms thereof, RNA, and any other type of polynucleotide which is a N-glycoside or C-glycoside of a purine or pyrimidine base, or modified purine or pyrimidine base or a basic nucleotide. The polynucleotide may encode promoter regions, operator regions, structural regions, termination regions, combinations thereof or any other genetically relevant material.

"Substitute" linkages are defined herein as conventional alternative linkages such as phosphorothioate or phosphoramidate, that are synthesized as described in the generally available literature. Not all linkages in a polynucleotide need to be identical. The polynucleotides of the invention may contain one or more "substitute" linkages as is generally understood in the art. Some of these substitute linkages are non-polar and contribute to the desired ability of the polynucleotide to diffuse across a membrane. Other substitute linkages contribute to the increased or decreased biodegradability of the polynucleotide. Biodegradability will be affected, for example, by increased or decreased nuclease sensitivity.

"Analogue purines" and "analogue pyrimidines" are those generally known in the art, many of which are used as chemotherapeutic agents, containing modifications in the sugar moiety of the polynucleotide. Examples of the analogue purines and pyrimidines are those wherein one or more of the hydroxyl groups are replaced with halogen or aliphatic groups, or are functionalized as ethers, amines, and the like, or wherein the ribose or deoxyribose is replaced with other functionally equivalent structures. Modifications in the base moiety include alkylated purines or pyrimidines, acylated purines or pyrimidines, or other heterocycles. In particular, the sugar-phosphate backbone of the polynucleotide may be replaced with a non-carbohydrate backbone such as a peptide or other type of polymer backbone (Nielsen, P. E., et al., Science 254:1497 (1991)).

The computed molecular weight for an ideal dendrimer containing no incomplete reaction products or side reaction products is the molecular weight. However, during the course of a synthesis some incomplete products or side-products usually arise. "Average molecular weight" as used herein refers to a hypothetical molecular weight of an ideal dendrimer but it should be noted that in practice deviations from this average molecular weight may occur, and molecules of various molecular weights lower and higher than this values are present in some proportion.

"Hydrodynamic radius" as used herein refers to the apparent radius of a single dendrimer in aqueous solutions. It can be estimated by those skilled in the art using gel permeation chromatography or laser light scattering.

"Functional component" as used herein includes DNA-masking components, cell recognition components, charge-neutralization and membrane-permeabilization components, and subcellular-localization components.

"DNA-masking component" as used herein refers to a molecule capable of masking all or part of a polynucleotide to increase its circulatory half-life by inhibiting attack by degrading reagents such as nucleases present in the circulation and/or interfering with uptake by the reticuloendothelial system.

"Membrane-permeabilizing component" as used herein refers to any component that aids in the passage of a polynucleotide across a membrane. Thus, this term encompasses in part charge-neutralizing components, usually polycations, that neutralize the large negative charge on polynucleotides, and enable the polynucleotide to traverse the hydrophobic interior of a membrane. Many charge-neutralizing components can act as membrane-permeabilizers. Membrane-permeabilization may also arise from amphipathic molecules. A membrane permeabilizer is a molecule that can assist a normally impermeable molecule to traverse cellular membranes and gain entrance to the cytoplasm of the cell. A membrane permeabilizer may be a peptide, bile salt, glycolipid, phospholipid or detergent molecule. Membrane permeabilizers often have amphipathic properties such that one portion is hydrophobic and another is hydrophilic, permitting them to interact with membranes.

"Fusogenic peptide" as used herein refers to a peptide that when added to two separate bilayer membranes can bring about their fusion into a single membrane.

"Liposome" as used herein refers to small vesicles composed of amphipathic lipids arranged in spherical bilayers. Liposomes are usually classified as small unilamellar vesicles (SUV), large unilamellar vesicles (LUV), or multilamellar vesicles (MLV). SUVs and LUVs, by definition, have only one bilayer, whereas MLVs contain many concentric bilayers. Liposomes may be used to encapsulate various materials, by trapping hydrophilic molecules in the aqueous interior or between bilayers, or by trapping hydrophobic molecules within the bilayer. Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart an overall neutral charge, phosphate and sulfate based lipids contribute a negative charge, glycerol-based lipids are generally negatively-charged, and sterols are generally neutral in solution but have charged groups.

"Cell recognition component" as used herein refers to a molecule capable of recognizing a component on the surface of a targeted cell. Cell recognition components include antibodies to cell surface antigens, ligands for cell surface receptors including those involved in receptor-mediated endocytosis, peptide hormones, and the like.

"DNA-associating moiety" refers to a molecule or portions thereof that interact in a non-covalent fashion with nucleic acids. DNA-associating moieties include major- and minor-groove binders, DNA intercalators, and polycation among others. Major- and minor-groove binders are molecules thought to interact with DNA by associating with the major or minor groove of double-stranded DNA. DNA intercalators are planar molecules or planar portions of molecules thought to intercalate into DNA by inserting themselves between, and parallel to, nucleotide base pairs. Polycations are thought to associate with the negative charges on the DNA backbone. In addition, when a single-stranded DNA or RNA is used as the therapeutic strand, the complementary "linker strand" as described herein may functionally act as a "DNA-associating moiety".

The DNA associating moieties may be covalently linked through a "reactive group" to a functional component of this invention. These reactive groups are easily reacted with a nucleophile on the functional component. Such reactive groups (with their corresponding reactive nucleophiles) include, but are not limited to N-hydroxysuccinimide (e.g., amine), maleimide and maleimidophenyl (e.g., sulfhydryl), pyridyl disulfide (e.g., sulfhydryl), hydrazide (e.g., carbohydrate), and phenylglyoxal (e.g., arginine).

"Subcellular-localization component" as used herein refers to a molecule capable of recognizing a subcellular component in a targeted cell. Recognized subcellular components include the nucleus, ribosomes, mitochondria, and chloroplasts. Particular subcellular-localization components includethe "nuclear-localization components" that aid in carrying molecules into the nucleus and are known to include the nuclear localization peptides and amino acid sequences.

"Dendrimer polycation" as used herein refers to a three-dimensional, highly ordered oligomeric and/or polymeric compound formed by reiterative reaction sequences starting from a smaller molecule or designated initiator such as ammonia or pentaerythritol, among others, having a positively charged surface as described, for example, by Tomalia et al. (1990), supra.

The Composition

The composition of this invention is a self-assembling polynucleotide delivery systems comprising a polynucleotide; and a dendrimer polycation operatively coupled to the polynucleotide.

The Polynucleotide

The polynucleotide may be a single-stranded DNA or RNA, or a double-stranded DNA or DNA-RNA hybrid. Triple- or quadruple-stranded polynucleotides with therapeutic value are also contemplated to be within the scope of this invention. Examples of double-stranded DNA include structural genes, genes including operator control and termination regions, and self-replicating systems such as plasmid DNA, among others.

Single-stranded polynucleotides or "therapeutic strands" include antisense polynucleotides (DNA and RNA), ribozymes and triplex-forming oligonucleotides. In order to have prolonged activity, the therapeutic strand preferably has as some or all of its nucleotide linkages stabilized as non-phosphodiester linkages. Such linkages include, for example, phosphorothioate, phosphorodithioate, phosphoroselenate, or O-alkyl phosphotriester linkages wherein the alkyl group is methyl or ethyl, among others.

For these single-stranded polynucleotides, it may be preferable to prepare the complementary or "linker strand" to the therapeutic strand as part of the administered composition. The linker strand is usually synthesized with a phosphodiester linkage so that it is degraded after entering the cell. The "linker strand" may be a separate strand, or it may be covalently attached to or a mere extension of the therapeutic strand so that the therapeutic strand essentially doubles back and hybridizes to itself.

The linker strand may also have functionalities on the 3' or 5' end or on the carbohydrate or backbone that serve as functional components to enhance the activity of the therapeutic strand. For example, the phosphodiester linker strand may contain a targeting ligand such as a folate derivative that permits recognition and internalization into the target cells. If the linker is attached to its complementary therapeutic strand that is composed of degradation-resistant linkages, the duplex would be internalized. Once inside the cell, the linker will be degraded, thereby releasing the therapeutic strand. In this manner, the therapeutic strand will have no additional functionalities attached and its function will not be impeded by non-essential moieties. This strategy can be applied to any antisense, ribozyme or triplex-forming polynucleotide and it is used to deliver anti-viral, anti-bacterial, anti-neoplastic, anti-inflammatory, anti-proliferative, anti-receptor blocking or anti-transport polynucleotides, and the like.

A separate linker strand may be synthesized to have the direct complementary sequence to the therapeutic strand and hybridize to it in a one-on-one fashion. Alternatively, the linker strand may be constructed so that the 5' region of the linker strand hybridizes to the 5' region of the therapeutic strand, and the 3' region of the linker strand hybridizes to the 3' region of the therapeutic strand to form a concatenate of the following structure.

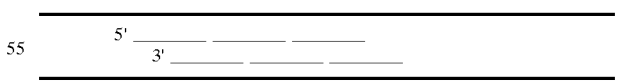

This concatenate has the advantage that the apparent molecular weight of the therapeutic nucleic acids is increased and its pharmacokinetic properties and targeting ligand:therapeutic oligonucleotide ratio can be adjusted to achieve the optimal therapeutic effect.

The Dendrimer Polycation

The dendrimer polycation is a three dimensional, highly ordered oligomeric and/or polymeric compound formed on a core molecule or designated initiator by reiterative reaction sequences adding the oligomers and/or polymers and providing an outer surface that is positively charged. These dendrimers may be prepared as disclosed in PCT/US83/02052 to the Dow Chemical Company, and U.S. Pat. Nos. 4,507,466,4,558,120, 4,568,737, 4,587,329, 4,631,337, 4,694,064, 4,713,975, 4,737,550, 4,871,779, and 4,857,599 to Tomalia, D. A., et al., or as described in the exemplary disclosure provided below. Typically, the dendrimer polycations comprise a core molecule upon which polymers are added. The polymers may be oligomers or polymers which comprise terminal groups capable of acquiring a positive charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dethiopyridyl, and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Oligomers and polymers suitable for the preparation of the dendrimer polycations of the invention are pharmaceutically-acceptable oligomers and/or polymers that are well accepted in the body. Examples of these are polyamidoamines derived from the reaction of an alkyl ester of an $\alpha,\beta$-ethylenically unsaturated carboxylic acid or an $\alpha,\beta$-ethylenically unsaturated amide and an alkylene polyamine or a polyalkylene polyamine, among others. Preferred are methyl acrylate and ethylenediamine. The polymer is preferably covalently bound to the core molecule.

The terminal groups that may be attached to the oligomers and/or polymers should be capable of acquiring a positive charge. Examples of these are azoles and primary, secondary, tertiary and quaternary aliphatic and aromatic amines and azoles, which may be substituted with S or O, guanidinium, and combinations thereof. The terminal cationic groups are preferably attached in a covalent manner to the oligomers and/or polymers. Preferred terminal cationic groups are amines and guanidinium. However, others may also be utilized. The terminal cationic groups may be present in a proportion of about 10 to 100% of all terminal groups of the oligomer and/or polymer, and more preferably about 50 to 100%.

The dendrimer polycation may also comprise 0 to about 90% terminal reactive residues other than the cationic groups. Suitable terminal reactive residues other than the terminal cationic groups are hydroxyl, cyano, carboxyl, sulfhydryl, amide and thioether, among others, and combinations thereof. However others may also be utilized.

The dendrimer polycation is generally and preferably non-covalently associated with the polynucleotide. This permits an easy disassociation or disassembling of the composition once it is delivered into the cell. Typical dendrimer polycations suitable for use herein have an about 2,000 to 1,000,000 MWave, and more preferably about 5,000 to 500,000 MWave. However, other molecule weights are also suitable. Preferred dendrimer polycations have a hydrodynamic radius of about 11 to 60 Å, and more preferably about 15 to 55 Å. However, other sizes are also suitable.

Good results are obtained with the present composition when the proportion of terminal cationic groups of the dendrimer polycation to the polynucleotide is about 1:4 to 25:1, and more preferably about 1:1 to 10:1. However, other proportions may also be utilized.

The composition may further comprise an agent selected from the group consisting of
1) DNA-masking components;
2) cell recognition components;
3) charge-neutralization and membrane-permeabilization components; and
4) subcellular localization components.

Each element in this system, including the dendrimer polycation, is preferably able to perform its indicated function and is also capable of assembling or disassembling with the polynucleotide as required. The composition may further comprise one or more of the above agents, and more preferably two or more of the agents. One embodiment of the system is shown in FIG. 13.

In this embodiment of the polynucleotide delivery system of the invention, NLS is a nuclear localization sequence, MD is a membrane-permeabilization component, and Ligand is a cell recognition component.

When the composition of the invention also comprises a membrane-permeabilizing agent, the proportion of this agent to terminal cationic groups of the dendrimer polycation is preferably about 1:100 to 1:4, and more preferably about 1:50 to 1:8. However, other proportions are also suitable. The membrane-permeabilizing agent may be coupled to the dendrimer polycation by covalent or electrostatic forces. The composition of the invention may additionally contain a phospholipid which may be in the form of a liposome, a polycation such as a polyamine, and the like.

When the composition comprises a subcellular-localization agent, the proportion of the subcellular-localization agent to terminal cationic groups of the dendrimer polycation may be about 1:100 to 1:5, and more preferably about 1:80 to 1:20. However, other proportions are also suitable. The subcellular-localization agent may be coupled to the dendrimer polycation by covalent or non-covalent forces.

When the subcellular-localization agent is a nuclear localization agent, it may also contain a DNA-associating moiety such as a single stranded polynucleotide linker, a dendrimer polycation or a major- or minor-groove binder, that is operatively coupled to the nuclear localization agent, in which case the attachment to DNA is preferably non-covalent. The DNA-associating moiety may be an intercalating agent such as are known in the art. Examples of these are described below. The intercalating agent may be coupled to one or more ligands targeted to a receptor located on the eukaryotic cell surface. In this case, the ligand and the dendrimer polycation form a cell recognition agent capable of recognizing the eukaryotic cell, and the targeting ligand is also coupled to the dendrimer polycation. The intercalating agent is non-covalently coupled to the polynucleotide, and the ligand is preferably covalently coupled to the intercalating agent. A membrane-permeabilizing agent that is operatively coupled to the intercalating agent or the ligand may also be present. Additionally, the composition may also comprise a fusogenic polypeptide which is operatively coupled to the dendrimer polycation. This coupling may be covalent or non-covalent. The composition may also contain a DNA-associating moiety such as those described below.

When a ligand targeted to a receptor located on the eukaryotic cell surface is present in the composition, the proportion of cell targeting ligand to terminal cationic groups of the dendrimer polycation is preferably about 1:100 to 1:10, and more preferably about 1:80 to 1:25. However, other proportions are also suitable. Examples of preferred cell targeting ligands are vitamins, carbohydrates and polypeptides. However, other are also suitable. The polypeptide may comprise antibodies or fragments thereof having a predetermined specificity.

When a fusogenic polypeptide is coupled to the dendrimer polycation, the proportion of fusogenic polypeptide to terminal cationic groups of the dendrimer polycation is preferably about 1:100 to 1:4, and more preferably 1:80 to 1:10. However, other proportions are also suitable.

The composition may also contain a DNA masking agent which is capable of increasing the circulatory half-life of the polynucleotide. The DNA masking agent is operatively coupled to the dendrimer polycation by covalent or non-covalent forces. The DNA masking agent is, however, preferably non-covalently coupled to the polynucleotide. When the DNA masking agent is present in the composition, the proportion of the DNA masking agent to the terminal cationic groups of the dendrimer polycation is preferably about 1:33 to 1:3, and more preferably about 1:25 to 1:8. However, other proportions are also suitable.

Other particular forms of all these agents that may be added to the composition are described below.

The Functional Components (1) DNA-Masking Components

The DNA-masking element of this system is a molecule capable of masking all or part of the polynucleotide, thereby increasing its circulatory half-life by inhibiting attack by degrading reagents present in circulation or blocking uptake by the reticuloendothelial system.

In this invention, polyethylene glycol (PEG) can be covalently linked with a DNA-associating moiety by conventional methods as described below, and used as a DNA-masking component. The PEG may have a molecular weight of about 700 to 20,000 Daltons, preferably about 1800 to 6000 Daltons, and is preferably present in a ratio (molecules PEG:bp DNA) of about 1:4 to 1:100, and more preferably about 1:20.

Alternatively, the DNA may be masked by association with lipids. In one embodiment, the DNA is encased in standard liposomes as described, for example, in U.S. Pat. No. 4,394,448 to Szoka et al., the pertinent portion of which specification is incorporated herein by reference. In another embodiment, the DNA is incubated with a synthetic cationic lipid similar to those described in U.S. Pat. No. 4,897,355 to Epstein et al. These cationic lipids have the chemical formula

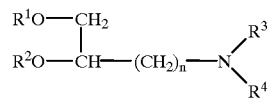

wherein
n is an integer from 1 to 8;
$R^1$ and $R^2$ are the same or different and are $(C_6-C_{24})$alkyl or alkenyl;
$R^3$ is hydrogen, or $(C_1-C_{10})$alkyl or alkylamine; and
$R^4$ is a positively charged linear or branched $(C_1-C_{30})$ alkyl or alkylamine, wherein one or more of the carbon atoms may be substituted with NR', wherein R' is hydrogen, or $(C_1-C_{10})$alkyl or alkylamine.

Preferred groups that can function as the —N—R' moiety are tris(aminoethyl)amine $(NH_2CH_2CH_2)_3N$, agmatine (decarboxyarginine) $H_2N(CH_2)_4C(=NH)NH_2$, 3-aminoethyl-1,3-propanediamine $H_2N(CH_2)_3NH(CH_2)_2NH_2$, 3-dimethylaminopropylamine $(CH_3)_2NH(CH_2)_3NH_2$, iminobis(N,N')dimethylpropylamine $NH((CH_2)_3N(CH_3)_2)_2$, iminobis (3-aminopropyl)-1,3-propanediamine, 1,4-bis(3-aminopropyl)piperazine, bis(propylamine) $(NH_2(CH_2)_3)_2NH$, spermidine, and spermine, among others. These groups are preferably attached to the lipid molecule through one of their nitrogen atoms.

In a specifically preferred embodiment, the synthetic cationic lipid is a synthetic cationic tail lipid having the chemical formula

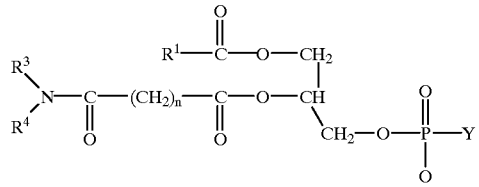

wherein
n is an integer from 6 to 24;
Y is selected from the group consisting of hydrogen, ethanolamine, choline, glycerol, serine, monomethoxy-polyethylene glycol, sialic acid, and inositol;
$R^1$ is $(C_6-C_{24})$alkyl or alkenyl;
$R^3$ is hydrogen, or $(C_1-C_{10})$alkyl or alkylamine; and
$R^4$ is a positively charged linear or branched $(C_1-C_{30})$ alkyl or alkylamine, wherein one or more of the carbon atoms may be substituted with NR', wherein R' is hydrogen, or $(C_1-C_{10})$alkyl or alkylamine.

Preferred groups that can function as the —N—R' moiety are tris(aminoethyl)amine $(NH_2CH_2CH_2)_3N$, agmatine (decarboxyarginine) $H_2N(CH_2)_4C(=NH)NH_2$, 3-aminoethyl-1,3-propanediamine $H_2N(CH_2)_3NH(CH_2)_2NH_2$ 3-dimethylaminopropylamine $(CH_3)_2NH(CH_2)_3NH_2$, iminobis(N,N')dimethylpropylamine $NH((CH_2)_3N(CH_3)_2)_2$, iminobis(3-aminopropyl)-1,3-propanediamine, 1,4-bis(3-aminopropyl)piperazine, bis(propylamine) $(NH_2(CH_2)_3)_2NH$, spermidine, and spermine, among others. These groups are preferably attached to the lipid molecule through one of their nitrogen atoms.

The above-described synthetic cationic lipids effectively mask the DNA when associated therewith. Without attempting to limit the invention in any way, it is believed that the lipids may form a monolayer structure that encapsulates the DNA in some fashion.

(2) Cell Recognition Components

The cell recognition element of this system is a molecule capable of recognizing a component on the surface of a targeted cell that is covalently linked with a DNA-associating moiety by conventional methods as described below. Cell recognition components include antibodies to cell surface antigens, ligands for cell surface receptors including those involved in receptor-mediated endocytosis, peptide hormones, etc. Specific ligands contemplated by this invention include carbohydrate ligands such as galactose, mannose, mannosyl 5-phosphate, fucose, sialic groups, N-acetylglucosamine or combinations of these groups as complex carbohydrates such as those found on glycolipids of the blood groups or on various secreted proteins. Other ligands include folate, biotin, various peptides that can interact with cell surface or intracellular receptors such as the chemoattractant peptide N-formyl-met-leu-phe SEQ ID NO:2, peptides containing the arg-asp-glycine sequence or cys-ser-gly-arg-glu-asp-val-trp SEQ ID NO:3 peptides, peptides that contain a cystine residue or that interact with cell surface protein such as the human immunodeficiency virus GP-120, and peptides that interact with CD-4. Other ligands include antibodies or antibody fragments such as those described by Hertler and Frankel (Hertler, A., and Frankel, A., J. Clin. Oncol. 7:1932 (1989)). The specificity of the antibodies can be directed against a variety of epitopes that can be expressed on cell surfaces including histocompatibility macromolecules, autoimmune antigens, viral, parasitic or bacterial proteins. Other protein ligands include hormones such as growth hormone and insulin or protein growth factors such as GM-CSF, G-CSF, erythropoietin, epidermal growth factor, basic and acidic fibroblast growth factor, and the like. Other protein ligands include various cytokines that work through cell surface receptors such as interleukin 2, interleukin 1, tumor necrosis factor, and suitable peptide fragments from such macromolecules.

(3) Membrane-Permeabilizing Components

The membrane-permeabilizing element of this system is a molecule that aids in the passage of a polynucleotide across a membrane. The liposomes and synthetic cationic lipids described above as DNA-masking components also may function as membrane-permeabilization components.

The membrane-permeabilizing components of this invention also include polycations that neutralize the large negative charge on polynucleotides. Polycations of this invention include polylysine, polyarginine, poly(lysine-arginine) and similar polypeptides, and the polyamines and polycationic dendrimers such as those described above and utilized in the examples and disclosed by Tomalia et al. (Tomalia, D. A., et al., (1990) supra). These dendrimers are a particularly preferred embodiment of this invention, since they, by themselves, in association with the polynucleotide, can substantially enhance the polynucleotide transfection efficiency as described above.

These non-linear polycationic cascade polymers combine the DNA-binding and delivery properties of polylysine and the lysomotropic effects of weak bases. Polyamidoamine (PAMAM) cascade polymers, a well-defined class of dendritic polymers synthesized from methyl acrylate and ethylene diamine as described by Tomalia et al., supra, are shown in the exemplary disclosure to be well-tolerated by cells and, when complexed to plasmids encoding reporter genes to mediate highly efficient transfection of a wide variety of cells in culture.

In a still more preferred embodiment, an amphipathic peptide such as GALA/SEQ ID NO:11 may be covalently attached to the cascade polymer (Subbarao, N. K., et al., "pH-Dependent Bilayer Destabilization byan Amphipathic Peptide", J. Biol. Chem. 26:2964 (1987)). This composition is also a most preferred embodiment of this invention, since it is shown in the exemplary disclosure to significantly enhance polynucleotide transfection efficiency in both primary cells and cell lines.

Another class of polycations are the cationic bile salts having the chemical formula

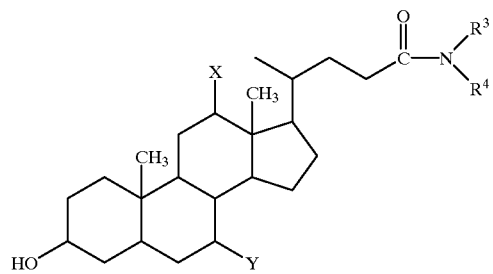

wherein

X and Y are independently H or OH;

$R^3$ is hydrogen, or $(C_1-C_{10})$alkyl or alkylamine; and $R^4$ is a positively charged linear or branched $(C_1-C_{30})$ alkyl or alkylamine, wherein one or more of the carbon atoms may be substituted with NR', wherein R' is hydrogen, or $(C_1-C_{10})$alkyl or alkylamine.

Preferred groups that can function as the —N—R' moiety are tris(aminoethyl)amine $(NH_2CH_2CH_2)_3N$, agmatine (decarboxyarginine) $H_2N(CH_2)_4C(=NH)NH_2$, 3-aminoethyl-1,3-propanediamine $H_2N(CH_2)_3NH(CH_2)_2$ $NH_2$, 3-dimethylaminopropylamine $(CH_3)_2NH(CH_2)_3$ $NH_2$, iminobis (N,N')dimethylpropylamine $NH((CH_2)_3N(CH_3)_2)_2$, iminobis(3-aminopropyl)-1,3-propanediamine, 1,4-bis(3-aminopropyl)piperazine, bis (propylamine) $(NH_2(CH_2)_3)_2NH$, spermidine, and spermine, among others. These groups are preferably attached to the bile salt through one of their nitrogen atoms.

In a different embodiment, the membrane-permeabilizing component of the invention is an amphipathic cationic peptide. Amphipathic cationic peptides are peptides whose native configuration is such that the peptide is considered to have a cationic face and a neutral, hydrophobic face. In a preferred embodiment, the peptide is a cyclic peptide. Examples of the amphipathic cationic cyclic peptides of this invention are gramicidin S, and the tyrocidines. The peptide may also contain some or all of the amino acids in the D configuration as opposed to the naturally occurring L configuration. The chemical structure of gramicidin S is shown below.

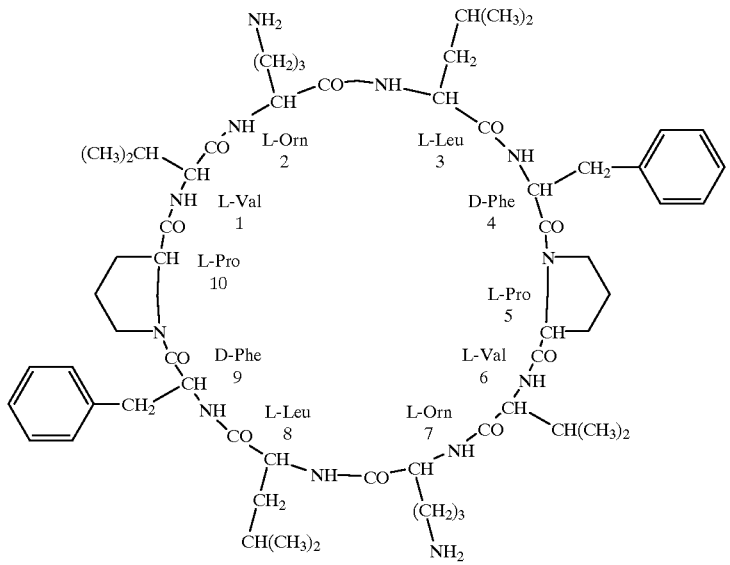

In a particularly preferred embodiment, the membrane-permeabilizing element includes, in addition to the amphipathic cationic cyclic peptides, either (1) a lipid, or (2) a simple polyamine, or both.

The lipid of the invention is an amphipathic molecule which is capable of liposome formation, and is substantially non-toxic when administered at the necessary concentrations either in native form or as liposomes. Suitable lipids generally have a polar or hydrophilic end, and a non-polar or hydrophobic end. Suitable lipids include without limitation egg phosphatidylcholine (EPC), phosphatidylethanolamine, dipalmitoylphosphatidylcholine (DPPC), cholesterol (Chol), cholesterylphosphorylcholine, 3,6,9-tri-oxaoctan-1-ol-cholesteryl-3e-ol, dimyristoylphosphatidylcholine (DMPC), and other hydroxy-cholesterol or aminocholesterol derivatives (see, e.g., Patel, K. R., et al., Biochim. Biophys. Acta 814:256 (1985)). The lipid is preferably added in the form of liposomes and the added polyamine is preferably spermine or spermidine.

The membrane permeabilizing elements, the cyclic peptide and optional phospholipid and polyamine, may be added to the composition simultaneously or consecutively. Preferably, the cyclic peptide is added first, and the phospholipid or polyamine later. The molar ratio of added cyclic peptide to polyamine is preferably of about 1:1 to about 1:3. The molar ratio of added cyclic peptide to phospholipid is preferably of about 1:1 to about 1:20.

(4) Subcellular-Localization Components

The subcellular-localization element of this system is a molecule capable of recognizing a subcellular component in a targeted cell, covalently linked with a DNA-associating moiety by conventional methods as described below. Particular subcellular components include the nucleus, ribosomes, mitochondria, and chloroplasts.

In a preferred embodiment of this invention, the subcellular-localization component is a nuclear-localization component. The nuclear-localization components include known peptides of defined amino acid sequences, and longer sequences containing these peptides. One known peptide sequence is the SV 40 large T antigen heptapeptide pro-lys-lys-lys-arg-lys-val SEQ ID NO:1. Other peptides include the influenza virus nucleoprotein decapeptide ala-ala-phe-glu-asp-leu-arg-val-leu-ser SEQ ID NO:4, and the adenovirus E1 a protein segment lys-arg-pro-arg-pro SEQ ID NO:5. Other sequences may be discerned from Dingwall et al. (Dingwall, C., et al., TIBS 16:478 (1991)).

In another embodiment, the subcellular-localization component is a lysosomal-localization component. A known component for targeting the lysosome is a peptide containing the lys-phe-glu-arg-gln SEQ ID NO:6 segment.

In yet another embodiment, the subcellular-localization component is a mitochondrial-localization component. A known component for targeting mitochondria is a peptide containing the sequence met-leu-ser-leu-arg-gln-ser-ile-arg-phe-phe-lys-pro-ala-thr-arg SEQ ID NO:7. However, other subcellular-localization components or agents are also suitable.

DNA-Associating Moieties

The DNA-associating moiety of this system refers to a portion of a functional component that interacts in a noncovalent fashion with nucleic acids. The moiety is covalently linked to the rest of the functional component by conventional means or as described below. DNA-associating moieties are preferably major-and minor-groove binders, DNA intercalators, or general DNA binders. In the case of single-stranded polynucleotides, the DNA-associating moiety may even be the linker strand as described above. In such a case the functional moiety, such as the cell-recognition or subcellular-localization component is covalently linked to the linker strand.

In one preferred embodiment, the DNA-associating moiety is a major- or minor-groove binder. The major- and minor-groove binders are moieties known to associate or "lay in" the major or minor groove of DNA. These binders include distamycin A and Hoechst dye 33258.

In another embodiment, the DNA-associating moiety is a nonspecific DNA binder such as a polycation. Polycations of this invention include polylysine, polyarginine, poly (lysine-arginine) and similar polypeptides, and the polyamines and the polycationic dendrimers.

In another preferred embodiment, the DNA-associating moiety is a DNA intercalator. DNA intercalators are planar polycyclic molecules such as ethidium bromide, acridine, mitoxantrone, oxazolopyridocarbazole, ellipticine and N-methyl-2,7-diazapyrenium, and derivatives thereof. In a particular preferred embodiment, the intercalator is a dimer consisting of two covalently linked planar polycyclic molecules. A planar polycyclic dimer moiety of this invention has the chemical formula

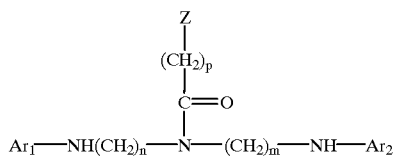

wherein
Z is a bond;
n and m are independently an integer of 1 to 20;
p is an integer of 0 to 20; and
$Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof, among others.

The values of n and m are important as they determine the spacing of the intercalated acridine monomers in the DNA. More preferred values of n and m are 3 and 4, respectively. Bis-acridine dimers, wherein $Ar_1$ and $Ar_2$ are both acridine, are preferred.

This preferred DNA-associating moiety may be covalently attached to a functional moiety, such as a cell recognition moiety, subcellular localization moiety, or membrane permeabilizing moiety as described above. The value of p determines the separation of the intercalator from the functional moiety. Preferred values for p are from 0 to 8.

The DNA-associating moiety may be covalently attached to multiple copies of one, or more than one, functional moiety. For example, a bis-acridine dimer may be attached to three galactose residues that bind to the hepatocyte asialoglycoprotein receptor.

A preferred method for attaching the DNA-associating dimer to the functional moiety involves a precursor having the chemical formula

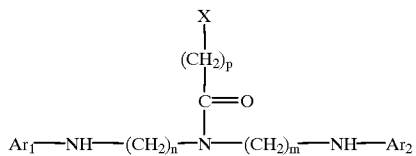

wherein
n and m are independently an integer of 1 to 20;
p is an integer of 0 to 20;
$Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof; and X is a reactive group selected from the group consisting of N-hydroxysuccinimide, maleimide, maleimidophenyl, pyridyl disulfide, hydrazide, and phenylglyoxal.

In one preferred embodiment, $Ar_1$ and $Ar_2$ are acridine, p is 3 and X is p-maleimidophenyl. This intercalating moiety is then coupled to the functional moiety through a sulfhydryl group on the functional moiety, for example, to obtain a bifunctional component having the chemical formula

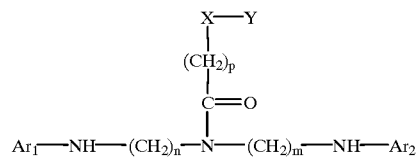

wherein
Y is a functional component;
n and m are independently an integer of 1 to 20;
p is an integer of 0 to 20;
$Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof; and
X is a reactive group selected from the group consisting of N-hydroxysuccinimide, maleimide, maleimidophenyl, pyridyl disulfide, hydrazide, and phenylglyoxal.

Biodegradable linkers such as peptides having the amino acid segment -lys-lys- may also be used in attaching the functional component to the intercalator.

In yet another embodiment of this invention, the planar polycyclic dimer has the chemical formula

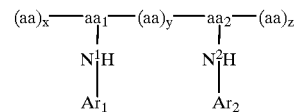

wherein
$Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof;
each aa is independently an amino acid;
x and z are integers independently selected from 1 to 100;
y is an integer from 0 to 5;
$aa_1$ and $aa_2$ are lysine residues; and
$N^1$ and $N^2$ are nitrogens from the $\epsilon$-amino groups of lysine residues $aa_1$ and $aa_2$.

The composition of the invention is suitably utilized for introducing a polynucleotide into a eukaryotic cell by contacting it with the cell. The introduction of the polynucleotide into the eukaryotic cell may be attained both in vitro and in vivo. In vivo, the composition may be administered in an amount comprising about 0.5 µg to 20 mg of the polynucleotide, and more preferably about 2.5 µg to 10 mg of the polynucleotide. However, other amounts may also be administered. The present method is suitable for introduction of polynucleotides into plant or animals cells, including human cells, both in vitro and in vivo.

The polynucleotide delivery system of the invention is useful in a therapeutic context. In therapeutic applications, the composition of the invention may be formulated for a variety of modes of administration, including systemic and topical or localized administration. Techniques and formulations generally may be found in Remington's Pharmaceutical Sciences, Mack Publishing Co., Easton, Pa., latest edition.

The composition of the invention is typically administered by the oral, transdermal, systemic or inhalation routes.

For systemic administration, parenteral administration such as injection is preferred, including intramuscular, intravenous, intraperitoneal, and subcutaneous. For treating disorders of the lung, administration of the polynucleotide delivery system may be done by inhalation or by installation of the system directly into the lung.

For injection, the composition of the invention may be formulated in the form of a liquid solution, preferably in physiologically compatible buffers such as Hank's solution or Ringer's solution, among others. In addition, the composition may also be formulated in solid form and sold and transported in this form, and redissolved or suspended immediately prior to use. Lyophilized forms are also included within the confines of this invention. The solid form may also be administered directly via a dry powder into the lungs, skin, gastrointestinal tract or muscle.

The systemic administration of the present composition may also be done by transmucosal or transdermal means, or the systems can be administered orally, or through intranasal or inhaled aerosols. For transmucosal or transdermal administration, penetrants appropriate to the barrier to be permeated are used in the formulation. Such penetrants are generally known in the art, and include, for example, for transmucosal administration of bile salts and fusidic acid derivatives. In addition, detergents may also be used to facilitate the permeation. Physical means such as high velocity impaction may also be used to facilitate penetration of the outer layer of the skin to position the complex in the epidermis. Transmucosal administration may be attained through nasal sprays, for example, or by means of suppositories.

For oral administration, the composition of the invention may be formulated into conventional oral administration forms such as capsules, tablets, and tonics.

For topical administration, the systems of the invention are formulated into ointments, salves, gels, or creams, as is generally known in the art. The topical or transdermal administration may be conducted by high velocity impaction administration to the skin surface. However, other means of transdermal or topical administration are also suitable.

Having now generally described this invention, the same will be better understood by reference to certain specific examples, which are included herein for purposes of illustration only and are not intended to be limiting of the invention or any embodiment thereof, unless so specified.

EXAMPLES

Example 1

Comparison of DNA-Dendrimer Complex- and DNA-Polylysine Complex-mediated Transfections To find better chemically-defined alternatives to the polyamine polymers such as polylysine, the hydrophilic branched polycation macromolecules also known as the Starburst™ Dendrimer microparticles (Tomalia et al., supra) were employed to form a complex with DNA or with DNA and the permeabilizing amphipathic peptide GALA/SEQ ID NO:11 (Parente, R., et al., Biochemistry 29:8720 (1990)). The complex was prepared by diluting 12 $\mu$g of pCLuc4 plasmid in 660 $\mu$l of HBS (20 mM Hepes, 150 mM NaCl, pH 7.4) in a polystyrene tube. Polylysine (Sigma Chemical Co.) or Starburst™ Dendrimer microparticles of the fifth generation (1 nmole) (Polysciences, Inc.) was dissolved in 340 $\mu$l of HBS and added slowly (dropwise) to the DNA solution. In these conditions, the positive charges from the epsilon amino groups of the polylysines or from the peripheral amines of the dendrimers are in 1.3-fold excess over the negative charges of the plasmids. When the peptide GALA/SEQ ID NO:11 was added, it was added so that the negative charges on GALA/SEQ ID NO:11 neutralized the excess charges on the dendrimer. The mixture was left to stand for thirty minutes after the last addition at room temperature and then 500 $\mu$l of the mixture was added to CV-1 cells. The transfection protocol was carried out as described above. In this experiment, the best transfection protocol was accomplished with the GALA/SEQ ID NO:11-dendrimer-DNA complex, followed by the dendrimer-DNA and then by polylysine-DNA. The results are shown in the table below.

TABLE

DNA-Dendrimer Mediated Transfection

| Condition | Luciferase activity Lights (units per mg cell protein) |
|---|---|
| Dendrimer-GALA/SEQ ID NO: 11-DNA | $(9 \pm 2) \times 10^5$ ($\underline{n} = 2$) |
| Dendrimer-DNA | $(5 \pm 2) \times 10^5$ ($\underline{n} = 2$) |
| Polylysine-DNA | $(2.7 \pm 0.1) \times 10^5$ ($\underline{n} = 2$) |

Example 2

Materials

PAMAM cascade polymers synthesized from an ammonia initiator core (generation 2 to 10) were obtained from Polysciences, Inc. (Warrington, Pa.) and are designated as Starburst™ Dendrimers. When needed, dendrimer solutions were concentrated using a Savant SC110 Speed Vac system. Similar results to those reported here are obtained when the cascade polymer was synthesized in our laboratory using the method of Tomalia et al. (Tomalia et al., supra) but starting from tris(2-aminoethyl)amine. The commercially available dendrimers should be analyzed on a calibrated gel permeation column to insure that the material conforms to the specified diameter, since some lots did not conform to specifications. Poly(L-lysine) hydrobromide with an average chain length of 115 lysine residues (pLys115) was obtained from Sigma Chemical Co. (St. Louis, Mo.). N-succinimidyl 3-(2-pyridyl) dithio)propionate (SPDP) was obtained from Pierce (Rockford, Ill.).

GALAcys (trp-glu-ala-ala-leu-ala-glu-ala-leu-ala-glu-ala-leu-ala-glu-his-leu-ala-glu-ala-leu-ala-glu-ala-leu-glu-ala-cs-ala-ala), a cysteine-containing analog of the amphipathic peptide GALA/SEQ ID NO:11, was synthesized at the UCSF Bioresources Center, purified and analyzed essentially as previously described for GALA/SEQ ID NO:11 (Subbarao et al., supra).

Example 3

Abbreviations

DME: Dulbecco's modified Eagle's medium.

EDTA: ethylenediaminetetraacetic acid.

HBS: Hepes buffered saline (10 mM Hepes; 150 mM NaCl, pH 7.3).

HEPES: N-(2hydroxyethyl)piperazine-N'-(2-ethanesulfonic acid).

MEM: minimal essential Eagle's medium.

MTT: 3-(4,5-dimethylthiazol-2-yl)-2,5-diphenyl-tetrazolium bromide.

TRIS: tris(hydroxymethyl) aminomethane

PAMAM SD54 and SD68: polyamidoamine Starburst™ Dendrimer

54 Å and 68 Å in diameter. pLys115: poly(L-lysine), 115 monomers average chain length.

Example 4

Modification of SD54 with GALAcys SEQ ID NO:8

The PAMAM dendrimer of the 5th generation (54 Å in diameter, SD54) was modified following Scheme 2 below.

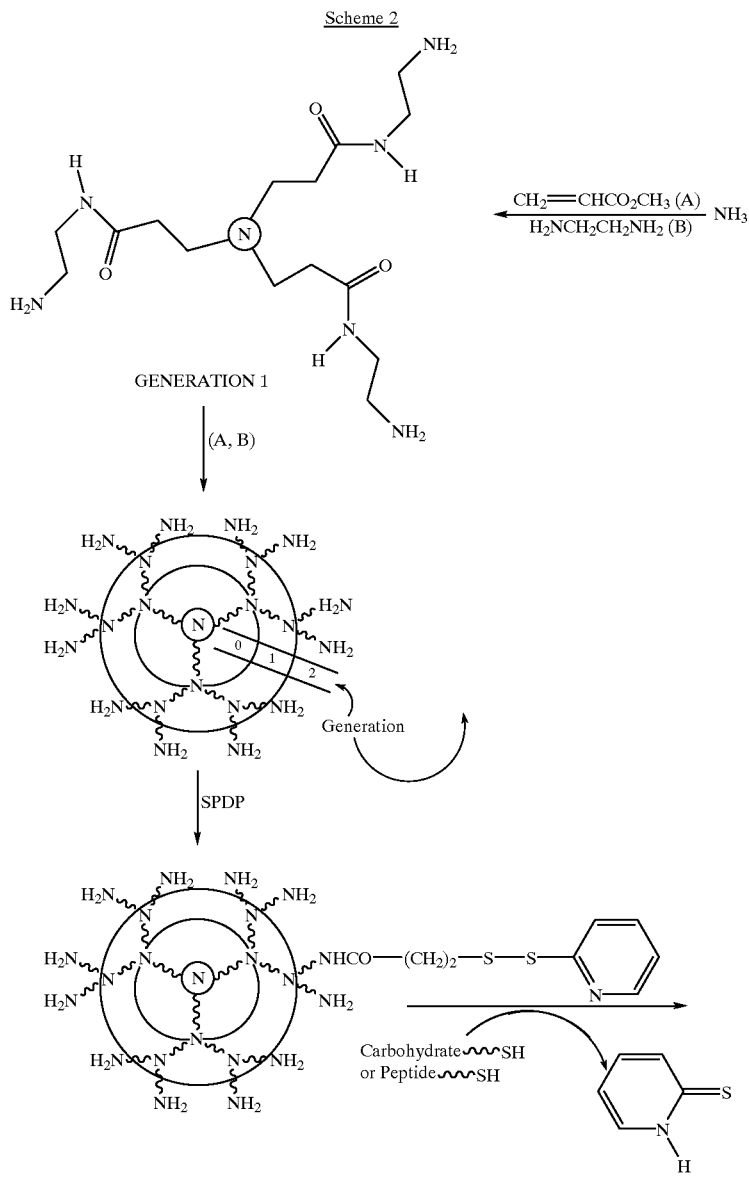

-continued

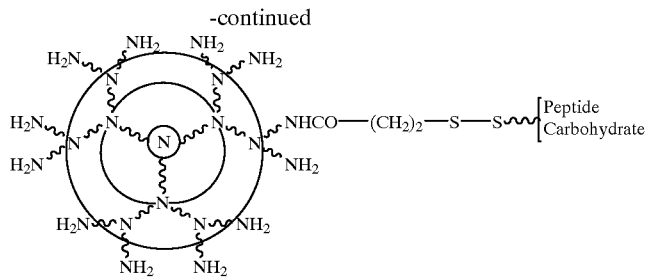

Example 5
Functionalization of SD54 with SPDP

The dendrimer (66 μmol terminal amines, 15 mg) in 0.5 ml of water was diluted with 0.75 ml of 0.1M phosphate buffer (pH 8.0) and 0.75 ml of a 15 mM solution of SPDP in ethanol was added dropwise. The reaction mixture was stirred for 1 hr. under Argon and fractionated on a Biogel P2 column (2.8×2 cm) eluted with 0.1M phosphate buffer (pH 7.4). The fractions containing 3-(2-pyridyidithio)propionate modified dendrimers (PDP-SD54 with an average of 16 dithiopyridine groups per particle) were pooled together and concentrated to a final volume of 3 ml.

Example 6
Reaction of PDP-SD54 with SEQ ID NO:8

One mililiter of a 10 mM solution of GALAcys SEQ ID NO:8 in a 0.1M phosphate buffer (pH 7.2) was added dropwise to 1 ml of the concentrated PDP-SD54 solution. The mixture was stirred overnight under Argon, and the GALA conjugate was purified by fractionating the reaction mixture on a calibrated Sephadex™ G75-120 column (2×90 cm) (Calibration kit Sigma MW-GF-70 containing Aprotinin (66,000) and Blue dextran (2,000,000)), and the column was eluted with 0.1M phosphate buffer (pH 7.4). The fractions containing the conjugate, which eluted with an apparent molecular weight of about 50,000, were pooled, concentrated and dialyzed against HBS (10 mM Hepes; 150 mM NaCl, pH 7.3). The dialyzed material was diluted with HBS to 1 mg of dendrimer/ml and sterile filtered through a 0.45 μm Millipore membrane.

Example 7
Expression Vectors

The plasmids pCLuc4 encoding firefly luciferase, and pCMV-βGal encoding β-Galactosidase were generous gifts from Dr. Cotten, M. (Institute of Molecular Pathology, Vienna, Austria) and Dr. Mc Gregor, G. (Howard Hughes Medical Institute, Houston, Tex.), respectively (De Wet, J. R., et al., "Firefly Luciferase Gene: Structure and Expression in Mammalian Cells", Mol. Cell Biol. 7:725 (1987); Mc Gregor, G. R., and Caskey, C. T., "Construction of Plasmids that Express *E.coli* β-galactosidase in Mammalian Cell Lines", Biotech. 7:1116 (1989)). Plasmids were grown in *Escherichia coli,* extracted by the alkali lysis technique, and purified by centrifugation in equilibrium CsCl gradients. The purity of the plasmids was checked by electrophoresis on a 0.8% agarose gel and the DNA concentration was determined form the absorbance at 260 nm.

Example 8
Preparation of Complex

A typical complex was made by diluting 6 μg of plasmid DNA into 33 μl of HBS in a polystyrene tube. The polycation and/or its GALA/ASEQ ID NO:11-functionalized derivative (2–160 μg) were diluted in 170 μl of HBS and added dropwise to the DNA. When the addition was completed the solution was gently mixed. The formation of the polycation-DNA complex was shown by a gel retardation assay; samples (30 μl) were electrophoresed through a 0.8% agarose gel using a Tris-Acetate-EDTA buffer system (pH 8.0) and DNA was visualized using ethidium bromide staining.

Example 9
Cells and Transfection Protocol

The adherent cell lines CV-1 (Monkey fibroblast), HeLa (Human carcinoma), HepG2 (Human hepatoma) were provided by the UCSF-cell culture facility. The cells were plated at a density of about $5 \times 10^5$ cells per 60 mm culture dish (Falcon) in 3 ml of DME-H21 containing 10% FCS and antibiotics (Penicillin, 100 units/ml and Streptomycin, 100 μg/ml). The cells were grown to half confluence at 37° C. in a humidified atmosphere containing 5% $CO_2$. In a typical experiment, cells were transfected in 1.5 ml of medium without serum by addition of 0.5 ml of HBS containing 6 μg of plasmid complexed with the indicated amount of polycation. The medium was removed 5 hrs. later and replaced by fresh medium containing 10% FCS. The cells were cultured for additional 24 or 48 hr. periods, and tested for reporter gene expression.

The suspension cell lines K-562 (Human erythroleukemia), EL-4 (Mouse lymphoma), and Jurkat (Human T-cells) were obtained from the UCSF-cell culture facility and grown in RPMI 1640 containing 10% FCS and antibiotics. For the transfection experiment, $1.2 \times 10^6$ cells in 1.5 ml of RPMI 1640 containing 7.5% FCS were introduced into each well of a 6-well plate or rotated in polypropylene tubes and transfected with 6 μg of DNA as described above. The cells were transferred 5 hrs. later to fresh medium containing 10% FCS. This was accomplished after centrifugation of the plate or tubes (1200 rpm for 5 min), and by removing 90% of the transfection medium and replacing it with fresh prewarmed medium. The cells were cultured for additional 24 or 48 hr. periods and tested for reporter gene expression.

Freshly isolated rat hepatocytes were obtained from Dr. Bissel, M. (Liver Center, UCSF) and plated at a density of $2 \times 10^6$ cells per 60 mm culture dish in 3 ml of an hepatocyte medium composed of 75% MEM and 25% Waymouth's medium containing 10% FCS, insulin (10 μg/ml), transferrin (10 μg/ml), dexamethasone (1 μM) and antibiotics (penicillin: 100 unit/ml; streptomycin: 100 μg/ml, and gentamycin: 25 μg/ml). The cells were grown at 37° C. in a humidified atmosphere containing 5% $CO_2$, and transfected 5 to 6 hrs. later as described above with 6 μg of plasmid in 2 ml hepatocyte medium containing 2% FCS. After an overnight incubation period, the transfection medium was removed and replaced with 3 ml fresh hepatocyte medium containing 2% FCS. The cells were further cultured for 24 hrs. and tested for reporter gene expression.

β-galactosidase gene expression was detected 24 hrs. after transfection by histochemical staining of the cells using X-Gal (Lim, K., and Chase, C.-B.,supra). Luciferase reporter gene expression was quantitated 48 hrs. after transfection on cell lysates by measuring the light emission with a bioluminometer (Analytical bioluminescence, San Diego, Calif.) in the presence of luciferin and ATP (Brasier, A. R., et al., "Optimized use of the Firefly Luciferase Assay as a Reporter Gene in Mammalian Cell Lines", Biotech. 7:1116 (1989)).

Example 10
Toxicity Assay

The effects of the cascade polymers on cell growth were assessed by measuring total protein content after transfection as well as by using a colorimetric dye reduction assay (Mosmann, T. R., "Rapid Colorimetric Assay for cellular Growth and Survival: Application to Proliferation and Cytotoxycity Assays", J. Immunol. Methods 65:55 (1983)). The effect of the 6th generation dendrimer (68 Å in diameter, SD68) was compared to the effect of polylysine (pLys115). The polycations were added to the cells with or without plasmid DNA at a ratio of 10 terminal amines of the polycation per nucleotide. The cells were plated at a density of about $5 \times 10^4$ cells per well in 300 μl of DME H-21 in 96 wells trays. After an overnight culture at 37° C. in a 5% $CO_2$ humidified atmosphere, the cells were incubated in triplicates with 200 μl serum-free medium containing 0 to 60 μg of pLys115 or SD68. After 5 hrs., the medium was replaced with 200 μl of fresh DME H-21 containing 10% FCS and the cells were cultured for an additional 48 hrs. Then, 10 μl of 3-(4,5-dimethylthiazol-2-yl)-2,5-diphenyltetrazolium bromide (MTT, 5 mg/ml) were added per well and allowed to react for 2 hrs. at 37° C. Solubilizing solution (0.4 N HCl in isopropanol, 200 μl) was added and the plate incubated for 30 min at room temperature. The absorbance was measured at 570 nm using an automatic ELISA plate reader (MR 700, Dynatech Laboratories Inc.), and corrected for background absorbance obtained on cells treated with 6M Guanidinium Hydrochloride (100% death). The results were expressed as % reduction in cell viability=$\{1-[OD_{570}$ (treated cells)-background]/$[[OD_{570}$ (untreated cells)-background]$\} \times 100$.

Example 11
Synthesis and Characterization of Modified Cascade Polymers

The dendrimer was used to attach functional groups to polynucleotides such as DNA to create gene delivery vehicles. The 5th generation PAMAM dendrimer was linked to GALAcys SEQ ID NO:8, a cysteine-containing analog of the amphipathic peptide GALA/SEQ ID NO:11, by using standard SPDP coupling chemistry (Carlsson, J., et al., "Protein Thiolation and Reversible Protein-Protein Conjugation. N-Succinimidyl 3-(2-pyridyidithio) Propionate, a New Heterobi-functional Reagent", Biochem. J. 173:723 (1978)) as shown in Table 1 below.

TABLE 1

Synthesis, Physical Characteristics and Functionalization of PAMAM Cascade Polymers

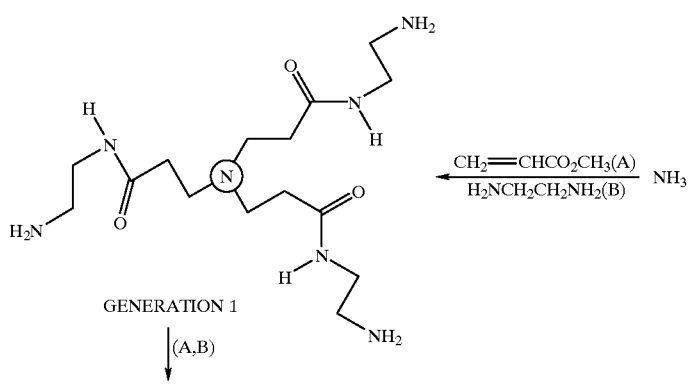

TABLE 1-continued

Synthesis, Physical Characteristics and Functionalization of PAMAM Cascade Polymers

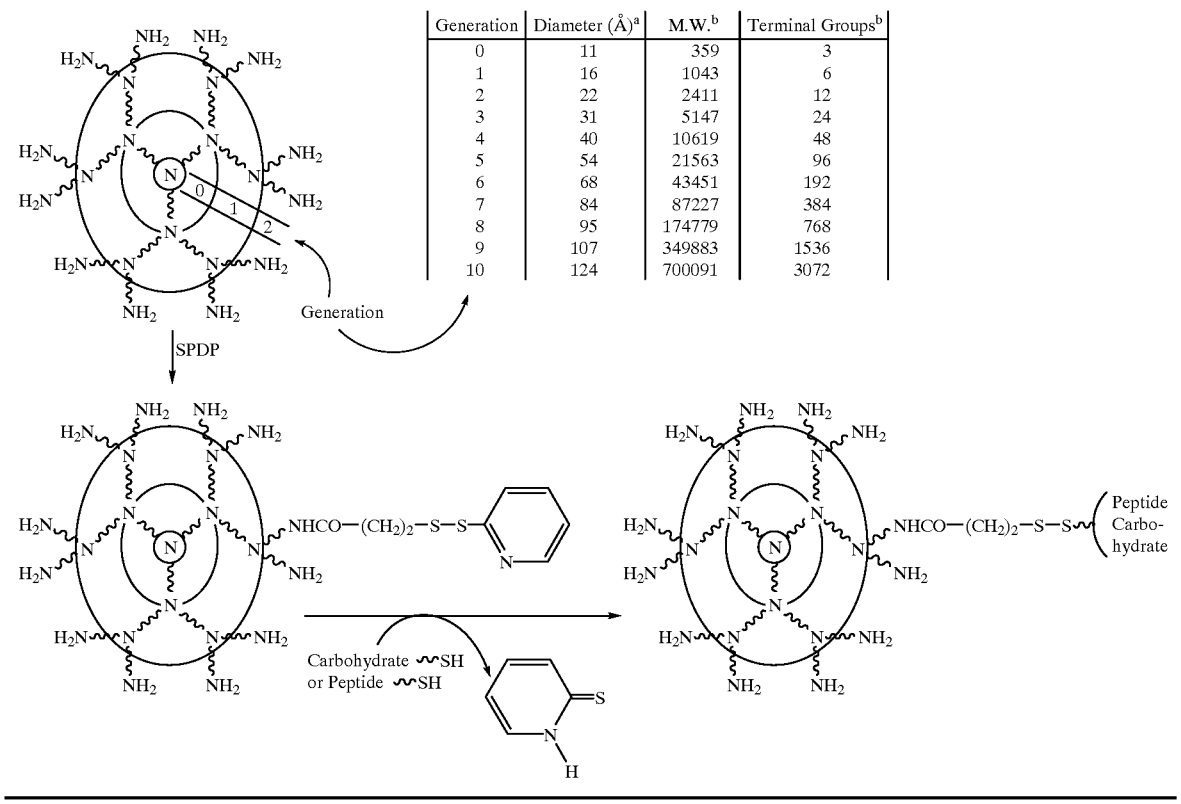

| Generation | Diameter (Å)[a] | M.W.[b] | Terminal Groups[b] |
|---|---|---|---|
| 0 | 11 | 359 | 3 |
| 1 | 16 | 1043 | 6 |
| 2 | 22 | 2411 | 12 |
| 3 | 31 | 5147 | 24 |
| 4 | 40 | 10619 | 48 |
| 5 | 54 | 21563 | 96 |
| 6 | 68 | 43451 | 192 |
| 7 | 84 | 87227 | 384 |
| 8 | 95 | 174779 | 768 |
| 9 | 107 | 349883 | 1536 |
| 10 | 124 | 700091 | 3072 |

[a]From Polysciences
[b]From reference 16

Modified from Tomalia et al.'s Reference

The dendrimer was successively functionalized with the heterobifunctional reagent SPDP and reacted with an excess of GALAcy/SEQ ID NO:8. The resulting conjugate was eluted from a calibrated Sephadex™ G75-120 column with an apparent molecular weight of about 50,000 Daltons. This suggests the presence of about 10 GALA GALAcys/SEQ ID NO:8 residues per dendrimer. An average of 13 GALA residues per dendrimer were quantified using a molar extinction coefficient for tryptophan of $\epsilon_{280\,nm}=5570M^{-1}\,cm^{-1}$ (pH 7.5). Since GALA GALAcys/SEQ ID NO:8 contains 8 negative charges per peptide, most of the unmodified amines on the conjugates are probably neutralized at pH 7.4. This is supported by the weak binding of the GALA-dendimer conjugate to DNA (vide infra).

Example 12
Binding of Cascade Polymers to DNA

Samples (30 μl) of polycation-pCMV-βGal complexes were incubated for 20 min and electrophoresed through a 0.8% agarose gel using a Tris-Acetate-EDTA buffer system (pH 8.0). The complexes were formed by mixing 6 μg of pCMV-βGal plasmid diluted in 330 μl HBS with the following agents in 170 μl HBS.

lane 1: pCMV-βGal alone;
lane 2: 2 μg of pLys115;
lane 3: 4 μg of pLys115;
lane 4: 4 μg of SD68;
lane 5: 6 μg of SD68;
lane 6: 4 μg of SD54 provided by the GALA/SEQ ID NO:11-SD54 conjugate;
lane 7: 160 μg of SD54 provided by the GALA/SEQ ID NO:11-SD54 conjugate;
lane 8: 4 μg of SD54 provided by an equimolar mixture of SD54 and GALA/SEQ ID NO:11-SD54.

After the electrophoresis was completed the gel was stained with ethidium bromide to visualize DNA.

The PAMAM dendrimers bind to DNA as demonstrated by retention of the complex at the point of application on an agarose electrophoresis gel as shown in FIG. 1. Both the polylysine (lanes 2 and 3) and the cascade polymer (lanes 4 and 5) were able to retard and immobilize the DNA on the gel. Gel retardation is a result of electrostatic and steric effects and suggests the formation of a charge complex between the positively-charged dendrimers and the anionic DNA. Because dendrimer terminal amines have lower $PK_a$ than lysine $\epsilon NH_2$ (see discussion), the dendrimer was slightly less effective in inducing gel retardation than polylysine as shown in FIG. 1. With polylysine total retention of the plasmid was observed at a 1:1 $\epsilon NH_2$ to nucleotide ratio (lane 3) whereas with the dendrimer total retention occurred at about 1.5:1 terminal $NH_2$ to nucleotide ratio (lane 5). The exact ratio of total retention varied by one dilution factor among experiments. The GALA/SEQ ID NO:11-dendrimer conjugate did not immobilize the DNA and affected only slightly the migration of the plasmid even when used in large excess over the DNA (lanes 6 and 7). A combination of GALA/SEQ ID NO:11- dendrimer conjugate and unmodified dendrimer (1:1 ratio, as used in the transfection assays) partially retained the plasmid (lane 8).

Example 13

Optimization of the Complex for Transfection

CV-1 cells (500,000 cells per 60 mm dish) were transfected in duplicate with increasing amounts of pCLuc4 (0.1 to 6 μg) complexed to SD68. In FIG. 3, the complexes were formed by adding the dendrimer dissolved in 170 μl HBS to the DNA in 330 μl HBS; (□), complexes were first formed by adding 25 μg of SD68 on 6 μg of pCLUC4 and then diluted in HBS to the stated amount of DNA; (○), the plasmid was first diluted in HBS and 25 μg of SD68 were added; (Δ), a non-luciferase containing plasmid was added to the diluted pCLuc4 plasmid to keep the total amount of DNA constant at 6 μg/330 μl and then 25 μg off SD68 were added. Luciferase expression was measured 48 hrs. post transfection as described in Table 2 below. Each value is the mean ± range of duplicate determinations.

An unexpected finding of this work is that the PAMAM cascade polymers can by themselves transfect DNA (e.g., plasmids encoding reporter genes) into cells in culture. The results are shown in Table 2 below, and in FIGS. 2 to 4.

primary amines]≦[nucleotides]) the cells were only poorly transfected by the complexes.

In the concentration range tested, the large diameter dendrimers (Ø≧40 nm), mediated better transfection efficiencies than the smaller ones. Luciferase expression increased by 2 to 3 orders of magnitude when the diameter of the complex-forming dendrimer was increased from 40 Å (generation 4) to 54 Å (generation 5). This can be best appreciated from examining the data on a three dimensional plot (see, FIG. 2). Maximal levels of transfection were obtained ($\geq 10^{10}$ LU/mg cell protein) with the dendrimer of the 6th generation (SD68, 68 Å diameter) at a ratio of 6 primary amines per nucleotide. With these conditions, luciferase expression in CV-1 cells was about a 100-fold greater than that obtained with an equivalent amount of polylysine 115 (see, Table 2 above) and a 100-fold greater than that obtained with the cationic lipid DOTMA (Legendre, J. Y., and Szoka, F. C., "Delivery of Plasmid DNA into Mammalian Cell Lines using pH-Sensitive Liposomes: Comparison with Cationic Liposomes", Pharm. Res. 9:1235 (1992)).

The optimized conditions were tested in 10 separate experiments in CV-1 cells, and luciferase activities between $2 \times 10^9$ and $3 \times 10^{10}$ LU/mg of cell proteins were obtained. When CV-1 cells were transfected with dendrimer in medium containing 10% FCS, the luciferase expression was decreased by about two fold, whereas expression decreased by 50 fold in the case of DOTMA (Legendre et al., supra).

TABLE 2

Influence of Amount and Size of PAMAM Cascade Polymer Complexed to pCLuc4 Plasmid on Luciferase Reporter Gene Expression in CV-1 Cells

| Generation | Ø (Å) | 0.5 | 1 | 3 | 6 | 10 | 16 | 25 |
|---|---|---|---|---|---|---|---|---|
| 10 | 124 | $(2.4 \pm 0.3)10^3$ | $(2.8 \pm 0.2)10^3$ | $(7.7 \pm 0.6)10^6$ | $(1.4 \pm 0.07)10^7$ [91%][a] | $(8.4 \pm 0.6)10^6$ [76%] | $(1.0 \pm 0.3)10^7$ [65%] | $(4.4 \pm 0.02)10^6$ [60%] |
| 9 | 107 | $(3.2 \pm 2.6)10^4$ | $(7.7 \pm 1.2)10^4$ | $(3.9 \pm 0.3)10^7$ | $(1.9 \pm 0.2)10^8$ [90%] | $(1.9 \pm 0.4)10^8$ [68%] | $(1.8 \pm 0.06)10^8$ [61%] | $(1.7 \pm 0.03)10^8$ [44%] |
| 8 | 95 | $(1.9 \pm 0.4)10^4$ | $(5.7 \pm 0.6)10^5$ [90%] | $(2.8 \pm 0.9)10^7$ [82%] | $(1.8 \pm 0.5)10^7$ [77%] | $(3.5 \pm 0.3)10^7$ [60%] | $(7.4 \pm 2.0)10^7$ [38%] | $(1.1 \pm 0.3)10^8$ [25%] |
| 7 | 84 | $(1.9 \pm 0.3)10^4$ | $(4.8 \pm 0.1)10^5$ | $(4.9 \pm 0.5)10^7$ [93%] | $(2.3 \pm 0.5)10^8$ [60%] | $(5.1 \pm 0.7)10^8$ [56%] | $(2.5 \pm 0.4)10^8$ [43%] | $(7.3 \pm 0.6)10^7$ [26%] |
| 6 | 68 | $(7.5 \pm 5.8)10^4$ | $(2.7 \pm 0.05)10^5$ | $(4.0 \pm 0.5)10^8$ | $(1.0 \pm 0.1)10^{10}$ [64%] | $(1.3 \pm 0.4)10^{10}$ [56%] | $(1.2 \pm 0.3)10^9$ [53%] | $(4.8 \pm 0.6)10^8$ [45%] |
| 5 | 54 | $(3.1 \pm 1.8)10^4$ | $(6.1 \pm 0.5)10^5$ | $(1.1 \pm 0.03)10^8$ | $(1.5 \pm 0.2)10^8$ [92%] | $(2.6 \pm 0.3)10^8$ [88%] | $(6.1 \pm 0.4)10^8$ [74%] | $(5.9 \pm 1.1)10^8$ [72%] |
| 4 | 40 | $(2.7 \pm 0.2)10^3$ | $(2.9 \pm 0.2)10^3$ | $(2.7 \pm 1.8)10^5$ | $(9.8 \pm 4.0)10^5$ | $(1.2 \pm 0.3)10^6$ | $(3.4 \pm 0.4)10^6$ | $(7.7 \pm 1.1)10^6$ |
| 3 | 31 | $(7.5 \pm 0.1)10^3$ | $(7.7 \pm 4.5)10^4$ | $(1.0 \pm 0.3)10^5$ | $(3.9 \pm 0.3)10^5$ | $(7.5 \pm 0.05)10^5$ | $(1.5 \pm 0.5)10^6$ | $(1.1 \pm 0.08)10^6$ |
| 2 | 22 | $(8.9 \pm 0.8)10^4$ | $(1.6 \pm 0.01)10^5$ | $(1.9 \pm 0.2)10^5$ | $(4.1 \pm 0.06)10^5$ | $(3.7 \pm 0.7)10^5$ | $(4.3 \pm 0.4)10^5$ | $(5.7 \pm 0.9)10^5$ |
| SD Generation | Ø (Å) | 0.5 | 1 | 3 Primary Amines/Nucleotides | 6 | 10 | 16 | 25 |
| pLys$_{115}$ | | 0.5 $(1.6 \pm 0.5)10^4$ | 1 $(1.7 \pm 0.6)10^5$ | 3 $(1.9 \pm 0.1)10^6$ [88%] | 6 $(7.3 \pm 2.3)10^6$ [57%] | 10 $(1.7 \pm 0.2)10^7$ [37%] | 16 $(1.9 \pm 0.6)10^7$ [11%] | 25 [0%] |

[a]Cell protein recovery compared to non-treated cells (no indication = 100% recovery).
Luciferase activity in the transfected cells (Light Units per mg of cell protein) is shown as the mean ± range of duplicates.
When transfection was toxic, the percentage recovery of cell protein in transfected cells compared to non-transfected cells is indicated in brackets.

The transfection activity was particularly high when an excess of terminal amines to nucleotide was used. To define the parameters controlling gene delivery and expression by the dendrimers, CV-1 cells were transfected with pCLuc4-dendrimer complexes and luciferase expression measured as a function of the diameter and amount of the dendrimer in the complex (see, Table 2 above). Transfection was sensitive to both factors. High luciferase expression required an excess of polycation. At low dendrimer input ([dendrimer A dose response of luciferase activity versus DNA input at a constant terminal amines/nucleotide ratio of 6:1 was constructed using the 68 Å diameter dendrimer (SD68), and is shown in FIG. 3). When the complex was first formed and then diluted to the stated amount of pCLuc4 plasmid, a linear decrease in expression of luciferase was observed (see, FIG. 3). If non-luciferase containing plasmid was used to dilute the luciferase plasmid and the dendrimer added, the transfecting activity also decreased in a linear fashion. When the plasmid was first diluted and a constant amount of dendrimer was added. In this case, the dendrimer/plasmid ratio increases with the dilution of the pCLuc4 plasmid, transfection activity decreased to a greater extent (see, FIG. 3).

Example 14
Transfection of Mammalian Cells with SD-68-DNA Complexes at Low Terminal Amines/Nucleotide Ratios Every cell type examined in this study could be transfected with PAMAM dendrimer-plasmid under conditions of excess terminal amines over nucleotides, including adherent and suspension cells as well as primary cultures and established lines (FIG. 4A). Transfection efficiency of the optimized complex was also studied by using the pCMV-βGal plasmid. β-galactosidase activity was detected by a histochemical stain 24 hrs. after transfection and transfected cells enumerated. These data are indicated as the percentage at the end of the bar on the graph (see, FIG. 4A). The different cell types studied differed in their ability to undergo transfection (up to 80% transfection in CV-1, less than 1% transfection in EL-4 and Jurkat). This variability is a general property shared by all gene delivery systems; the reason for such variable transfection among different cell types is not understood yet.

At the lower dendrimer input, the transfection efficiency of the dendrimer-DNA complexes was dramatically reduced (see, FIG. 4A and 4B). Reduced transfection activity with lower terminal amines/nucleotide ratios is similar to results seen with polylysines. Thus, the possibility that treatments that can increase transfection mediated by linear polycations could increase the dendrimer-mediated transfection was examined. Transfection was essentially insensitive to chloroquine (data not shown), but increased significantly when the fusogenic peptide GALA/SEQ ID NO:11 was attached to the (See, FIG. 4B).

Example 15
Enhancement of Transfection by Covalent Attachment of the Amphipathic Peptide GALAcys SEQ ID NO:8 to the Cascade Polymer The endosome disruptive effects of inactivated viral particles and of viral fusogenic peptides have been exploited to trigger or enhance polylysine-mediated gene transfer (Wagner, E., et al., "Coupling of Adenovirus to Transferrin-polylysine/DNA Complexes Greatly Enhances Receptor-Mediated Gene Delivery and expression of Transfected Genes", PNAS (USA) 89:6099 (1992); Wagner, E., et al., "Influenza Virus Hemagglutinin HA-2 N-terminal Fusogenic Peptides Augment Gene Transfer by Transferrin-polylysine/DNA Complexes: Toward a Synthetic Virus-Like Gene-Transfer Vehicle", PNAS (USA) 89:7934 (1992)). The 30-amino acid peptide GALA/SEQ ID NO:11 was designed to destabilize lipid bilayers in a pH-sensitive manner to mimic properties of viral fusogenic proteins (Subbarao, N. K., et al., supra). GALA/SEQ ID NO:11 was herein attached to the dendrimer to test whether it would increase transfection as do the viral particles or the viral fusogenic peptides. At a low terminal amines: nucleotide ratio, the transfection efficiency of the dendrimer-DNA complexes was low. However, transfection was significantly improved when 50% of the dendrimer in the complex was replaced for its GALA/SEQ ID NO:11- conjugate (see, FIG. 4B). Under these conditions, the conjugate can function at a low dendrimer/plasmid ratio (about 50:1 in these experiments). In the case of some cell types, such as K562, the GALA/SEQ ID NO:11-conjugate was as effective as when an excess of dendrimer was employed for transfection (see, FIGS. 4A and 4B). These results indicate that GALA/SEQ ID NO:11 enhances transfection, probably by catalyzing endosome leakage. At a dendrimer input where transfection was maximal, the expression was not further enhanced by GALA/SEQ ID NO:11. This may be because dendrimers display lysosomotrophic effects.

Example 16
Comparison of PAMAM Cascade Polymer and pLys115 Cytotoxicity

One index of the toxicity of the transfection procedure is the amount of cell protein obtained from the cultures following transfection. Treatments that resulted in a decrease in the yield of cell protein when compared to non-treated cells, are indicated in brackets in Table 2 above. In general, the dendrimer-DNA-induced cytotoxicity seemed to be controlled by the following three main parameters.

1) The diameter of the dendrimer.
2) The amount added.
3) Whether or not DNA was present.

The last factor can be better appreciated by comparing the toxicity of the dendrimer SD-68 to that of polylysine 115 on CV-1 cells in the presence and absence of plasmid DNA (see, FIG. 12). The overall cytotoxicity of SD68 was low when compared to that of pLys115. In the absence of DNA, the $LD_{50}$ of pLys115 on CV-1 cells was 25 µg/ml whereas the $LD_{50}$ of SD68 was greater than 300 µg/ml. In the presence of plasmid DNA (ratio of 10:1 primary amines of polycation: nucleotide), the cytotoxicity of pLys115 was not affected while that of SD68 was increased ($LD_{50}$ of SD68-DNA=100 µg/ml) but was still significantly lower than that of pLys115.

When optimized transfection conditions were utilized, the concentration of SD68 was 12.5 µg/ml, a level of dendrimer that induced an about 35% decrease in dye reduction (see, FIG. 5) as well as in cell protein recovery (see, Table 2 above). According to the cell protein recovered at the end of the assay, the transfection with SD68-DNA complexes was reasonably well-tolerated by all of the different cell types tested (Protein recovery ≧60%).

Example 17
Discussion of Results

Polycationic polymers such as polylysines have been extensively used for gene transfer into animal cells (Felgner, P. L., Adv. Drug Delivery Rev. 5:163 (1990)). The polylysine-based vectors have a high delivery capacity, but an efficient transfection of the target cells occurs only in the presence of endosome disrupting or lysosomotrophic agents (Cotten, M., et al., "Transferrin-Polycation-Mediated Introduction of DNA into Human Leukemic Cells: Stimulation by Agents that Affect the Survival of Transfected DNA or Modulate Transferrin Receptor Levels", PNAS (USA) 87:4033 (1990); Cotten, M., et al., "High Efficiency Receptor-Mediated Delivery of Small and Large (48 Kb) Gene Constructs Using the Endosome Disruption Activity of Defective or Chemically- Inactivated Adenovirus Particles", PNAS (USA) 89:6094 (1992)). The polycationic polymers of Examples 1 to 16 exhibit the combined delivery capacity of polylysines and the transfection capacity of a virus.

The PAMAM cascade polymers used herein are derived from an ammonia core and —$CH_2CH_2CONHCH_2CH_2N$ units resulting from successive additions of methyl acrylate and ethylene diamine as shown in Table 2 above. The controlled step-growth propagation of this structure produces increasingly higher generations of polymers with dimensionally precise surfaces and with a defined number of surface groups (Tomalia, D. A., et al., supra). The diameter of the higher generation dendrimers is similar to the diameter of the histone core of chromatin (about 70 Å) and might act as a scaffold to condense the DNA (Richmond, T. J., et al., "Structure of the NucleosomeCore Particle at a 7 Å Resolution", Nature 311:532 (1984)). Thus, the PAMAM dendrimes, differ from polylysines in their well-characterized formula and structure, their branching, and the low $pK_a$ of their terminal amines ($pK_a$=6.9) and internal amines ($pK_a$=3.9) (Tomalia, D. A., et al., supra).

The efficient cell internalization of DNA when associated with polycations may be due to a zipper-like association of the excess positive charges of the polycation-DNA complex with negatively charged cell-surface groups. This interaction may result in adsorptive endocytosis and membrane destabilization, such as has been proposed by Behr for cationic liposomes-DNA complexes (Behr, J.-P., "Synthetic Gene-Transfer Vectors", Acc. Chem. Res. 26:274 (1993)). Indeed, the DNA binding abilities of polylysine and the dendrimer, studied by gel retardation, are somewhat similar (see, FIG. 1). To increase membrane destabilization after endocytosis, the membrane destabilizing peptide GALA/ SEQ ID NO:11 was attached to the dendrimer.

When tested for plasmid delivery and transfection, the unmodified PAMAM dendrimers displayed excellent characteristics. The transfection efficiency was seen to depend on the size and amount of the dendrimer in the DNA-dendrimer complex. Most notably, a dramatic increase in transfection was observed when the diameter of the dendrimer was increased from 40 Å (generation 4) to 54 Å (generation 5). The reason for this threshold effect is still unclear but may be related to the diameter and structure of the polymer. Although generation 3 PAMAM dendrimers resemble a starfish, by generation 5 they have a spheroidal form of about 54 Å in diameter (Tomalia, D. A., et al., supra). This spherical shape might serve as a highly structured core to either favorably constrain the DNA, such as occurs in chromatin (Richmond, T. J., et al., supra). Alternatively, the spherical form may be more efficient at destabilizing membranes than either the lower generation dendrimers or linear polycations.

The PAMAM cascade polymers also differ from polylysines in the $pK_a$ of their primary and interior amino groups ($pK_a$'s=6.9, 3.9). This property may also be important for transfection. At physiological pH, the PAMAM dendrimers are only partially protonated and should display lysosomotrophic effects similar to weak bases (Stenseth, K. and Thyberg, J., "Monensin and Chloroquine Inhibit Transfer to lysosomes of Endocytosed Macromolecules in cultured Mouse Peritoneal Macrophages", Eur. J. Cell. Biol. 49:326 (1989)). In addition, the interior tertiary amino groups, which constitute the branching of the dendrimer, have a $pK_a$ of 3.9 and might also contribute to the lysosomotrophic effect. Thus, the dendrimer should be capable of buffering endosomal acidification after cellular uptake of the complex. The putative lysosomotrophic properties of the PAMAM dendrimers may explain why an excess of dendrimers is required for high transfection whereas an excess of polylysines does not increase transfection (see, Table 2 above). The side chain amino groups ($pK_a$=9 to 10) of polylysine are strongly charged at neutral pH and cannot buffer the acidification of the endosome. This is supported by the observation that the transfection efficiency of the dendrimer-DNA complex is not enhanced by chloroquine (data not shown). The transfection efficiency of the polylysine-DNA complexes, on the other hand, is usually dramatically enhanced in the presence of chloroquine (Cotten, M., et al. (1990), supra).

The complex composed of plasmid DNA and SD68 at a ratio of 6 terminal amines of SD68 per nucleotide displayed the best transfection activity. In these optimal conditions, there are about 320 SD68 particles per pCLuc4 plasmid however all the dendrimer particles may not be involved in complexes with DNA. As suggested above, the excess dendrimer may act as a lysosomotrophic agent. Above this optimal ratio, the system becomes less efficient. Increasing the amount of SD68 may decrease transfection efficiency because of toxicity associated with the complex. Alternatively, an increase in the amount of non-complexed dendrimer complex may compete with the DNA-dendrimer for putative binding sites on the cell surface. This would decrease the level of cell associated DNA and in this fashion decrease transfection efficiency.

Increasing the diameter of the dendrimer, while maintaining the 6:1 ratio, did not increase toxicity, but decreased the transfection efficiency. When observed under the optical microscope cells exposed to dendrimer-DNA complexes formed from greater than the 6th generation dendrimer exhibited large intracytoplasmic vacuoles. These size vacuoles are not observed in cells treated with complexes formed from dendrimers of the 6th or lower generations. It is not clear whether the vacuoles are related to the reduced transfection rates observed.

Toxicity was further examined by using the MTT dye reduction assay. The SD68 dendrimer is very well-tolerated by cells, much better than equivalent amounts of pLys115. The marked difference in toxicity between pLys115 and SD68 may be due to a difference in the ionization state of the particles. At physiological pH, polylysine bears more positive charges than the dendrimers and should have a stronger interaction with cell membranes. The toxicity of the dendrimer was significantly increased in the presence of plasmid DNA but remained less than that of the corresponding polylysine-DNA complexes.

The GALA/SEQ ID NO:11 peptide, a membrane destabilizer, was able to significantly increase the transfection activity of the complex when it was covalently attached to the dendrimer (see, FIG. 4B). GALA/SEQ ID NO:11 is a water soluble membrane destabilizer and its pH dependent interaction with membranes has been well studied (Subbarao, N. K., et al., supra); Parente, R. A., et al., "Association of a pH-Sensitive Peptide with Membrane Vesicles: Role of Amino Acid Sequence", Biochem. 29:8713 (1990) and references therein). Peptides with the GALA/ SEQ ID NO:11 motif have been attached by others to antibodies to increase their tumor cell retention and internalization (Anderson, D. C., et al., "Enhanced In Vitro Tumor Cell Retention and Internalization of Antibody Derivatized with Synthetic Peptides", Bioconjugate Chem. 4:10 (1993)). The fact that the dendrimer-GALA/SEQ ID NO:11 conjugates mixed with unmodified dendrimers in a 1:1 ratio enhance transfection shows that the dendrimers are excellent constituents of highly efficient transfection systems.

Starburst™ PAMAM Dendrimers based transfection procedures constitute simple and efficient methods for gene transfer into animal cells. The superior results obtained on a wide variety of cells (see, FIG. 4) show that the PAMAM Dendrimers, by themselves, are well suited for the direct delivery of genes to animals.

containing peptides were attached to the intercalator via a thiother linkage and the resulting peptide-intercalator associated with ds DNA via bis-intercalation of the acridines. Attachment of a nuclear localization peptide sequence to DNA using this reagent, enhances transfection in cultured cells.

The synthesis of MPB-bA is based upon a trifunctionalization of spermidine as shown in the following Scheme 3 below.

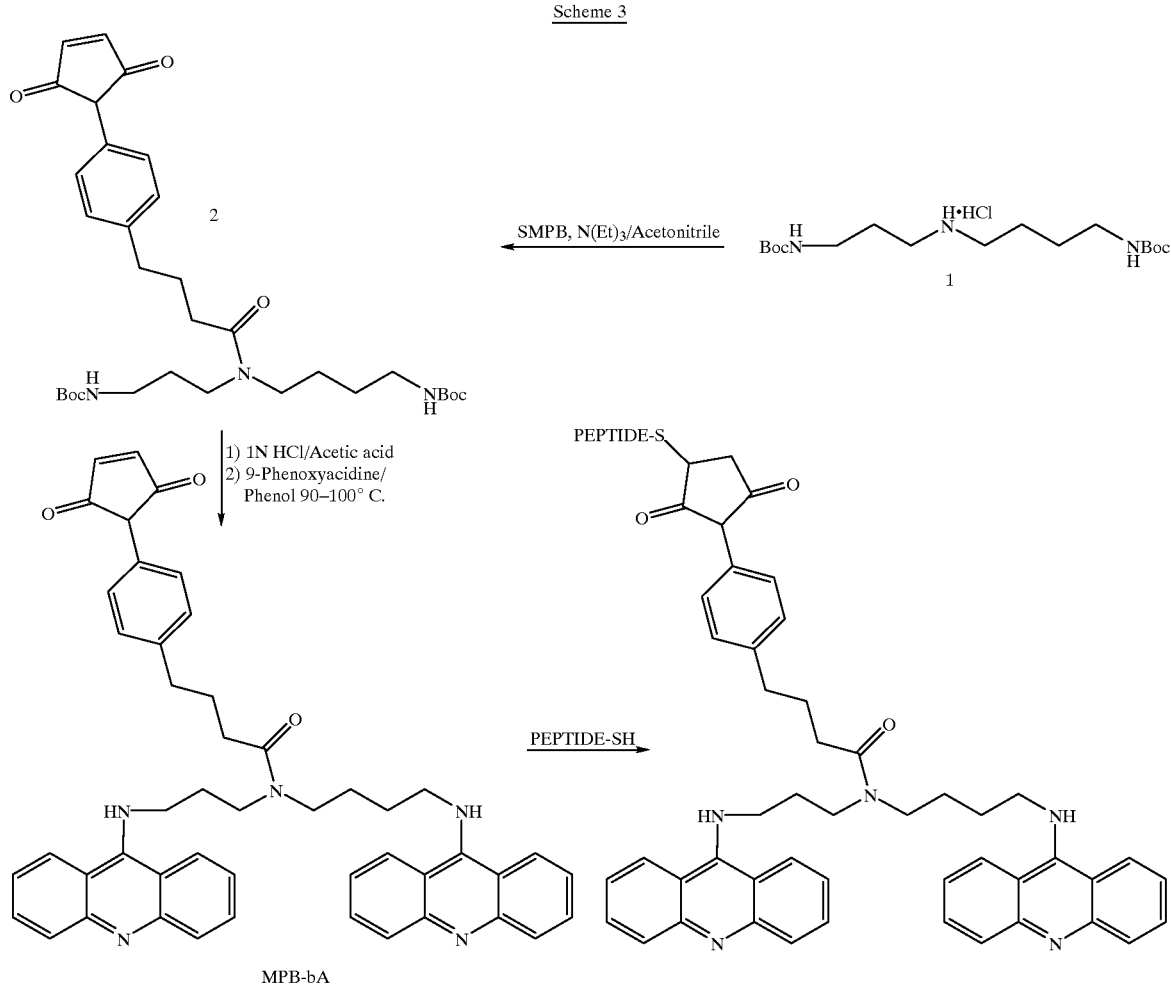

Scheme 3

MPB-bA

Example 18
Synthesis of MPB-bA

A bifunctional molecule consisting of a sulfhydryl reactive maleimide attached to a bis-acridine-spermidine (N4[p-(maleimidophenyl)butyryl]N$_1$, N$_8$(bis-9-acridinyl) spermidine (MPB-bA) was synthesized. The sulfhydryl N$_1$,N$_8$-bis(t-butoxycarbonyl) spermidine 1, the starting material, is a substrate suitable for selective N$_4$ acylation of spermidine (Bergeron, R. J., et al., Synthesis 689–692 (1989)). Compound 1 was successively N4-acylated with N-succinimidyl 4[p-(maleimidophenyl)butyrate (SMPB) as described by Kitogawa and Aikawa, deprotected, and the N$_1$,N$_8$ regenerated amines were reacted with 9-phenoxycaridine as described by Nielsen et al. to form a bis-acridine bearing a reactive maleimide (MPB-bA) (Kitawa, T., and Aikawa, T., J. Biochem. 79:233 (1976); Nielsen, P. E., et al., Bioconjugate Chem. 2:57 (1991)).

MPB-bA was precipitated in diethyl ether and purified by column chromatography on silica gel, and eluted with n-butanol/acetic acid/water (5:4:1 v/v).

Rf=0.28.

LSIMS: m/z=741.8 (M$^+$H).

A stable thioether bond forms when a sulfhydryl-containing peptide is reacted with the maleimide bearing intercalator as shown in Scheme 3 above. A sulfhydryl group may be attached to the N-terminal of the peptide with the reagent succinimidyl 3(2-pyridyldithio) propionate (Carlsson, J., et al., Biochem. 173:723 (1978)). Alternatively, the peptide may be synthesized with a cysteine residue at the appropriate location. The synthesis is robust and provides an overall yield of about 15%.

Example 19

Synthesis of 13-Amino Acid Peptides with Terminal Cys

To demonstrate that the MPB-bA could mediate peptide attachment to DNA, two 13-residue peptides were synthesized with an N-terminal cysteine. The first, SEQ ID NO:9 (cys-gly-tyr-gly-pro-lys-lys-lys-arg-lys-val-gly-gly) (WTcys), contained the SV40 large T antigen nuclear localization sequence. The second, SEQ ID NO:10 (cys-gly-tyr-gly-pro-lys-asp-lys-arg-lys-val-gly-gly) (cTcys), was a control peptide that mimics the mutation present in the SV40 (cT)-3 mutant, that is deficient for the transport of T antigen into the nucleus. These peptides were synthesized as described by Landford et al. (Landford, R. E., et al., Cell. 46:576 (1986)).

Example 20

Attachment of the 13-Amino Acid Peptides to MPB-bA

The peptides of Example 19 were reacted with MPB-bA as shown in the above Scheme 3. One mg of HPLC-pure peptide dissolved in 360 $\mu$l of a 0.2M phosphate buffer, and 1 mM EDTA, pH 7.2 were reacted with 1 mg of MPB-bA dissolved in 40 $\mu$l of methanol for 45 min with stirring under Argon. WTcysMPB-bA and cTcysMPB-bA were purified by gel filtration on a Biogel P2 column followed by C-18 reverse phase HPLC as described for the free peptides by Landford et al. (1986), supra, and lyophilized.

LSIMS: WTcysMPB-bA.

m/z=2118.9 (M$^+$H).

m/z=2140.7 (M$^+$Na).

cTcysMPB-bA.

m/z=2106.2 (M$^+$H).

m/z=218.4 (M$^+$Na).

The interaction of the resulting bis-acridinyl peptides with plasmid DNA, at a ratio allowing charge neutralization, led to a total inhibition of the electrophoretic mobility of the plasmid while equal amounts of the unconjugated peptides only partially retained the DNA (Results not shown).

The intercalation of the bis-acridinyl peptides into ds DNA led to the displacement of ethidium bromide from calf thymus DNA as shown in FIG. 6.

The binding constants of the various bis-acridines were computed from the competitive displacement of ethidium bromide, an intrinsic dissociation constant of 6.7×10$^6$M for ethidium bromide and the algorithm of Wolfe and Meehan (Reinhardt, C. G. and Krugh, T. R., Biochem. 17:4845 (1978); Wolfe, A. R. and Meehan, T., Mol. Biol. 223:1063 (1992)). These binding constants were compared to that of spermidine bis-acridine alone. As result of the loss of one of its positive charges, a slight but significant decrease in affinity was observed when the N$_4$ amino group of the spermidine bis-acridine was acylated as in MPB-bA. The conjugates formed by the cysteine-containing peptides and MPB-bA were found to bind DNA with affinity constants compatible with a bis-intercalation mechanism. The attachment of the positively charged peptides to MPB-bA partially restored the affinity as indicated in FIG. 6.

Ethidium bromide (19 $\mu$M) was mixed with calf thymus DNA (5.7 $\mu$M as nucleotide equivalents) in a 10 mM Tris-HCl buffer, 0.2M NaCl, pH 7.4 and increasing amounts of a bis-acridine derivative were added. The fluorescence elicited by the displacement of ethidium bromide was measured under the following conditions.

Excitation=540 nm; Emission=610 nm.

Fo: Fluorescence of free ethidium bromide (19 $\mu$M).

Fmax: Fluorescence of the ethidium-DNA complex alone (19 $\mu$M ethidium, 5.7 $\mu$M nucleotide).

F: Fluorescence of the ethidium-DNA complex in presence of the bis-acridine derivative.

i) The intrinsic fluorescence of the acridine occurs at 450 nm and does not interfere in this assay.
  ii) The concentration of the bis-acridine stock solutions was determined from the absorbance at 412 nm using a spermidine bisacridine standard.

Example 21

Transfection Efficiency of WTcysMPB-bA and cTcysMPB-bA

The transfection efficiencies of unmodified plasmids or plasmids mixed with either the WTcysMPB-bA or the mutant cTcysMPB-bA were determined. This functional assay is based on the following observations.

i) The transfection efficiency obtained with reconstituted viral envelopes increases when the encapsulated genes are co-delivered into the target cells with synthetic nuclear proteins composed of BSA linked to the SV40 large T antigen nuclear localization sequence (Kaneda, Y., et al., Science 243:375 (1989).
  ii) The SV40 virion particles microinjected into the cytoplasm of cultured cells are transported through nuclear pore complexes.

A plasmid encoding the bacterial luciferase gene, pCLuc4 plasmid, complexed to the MPB-bA peptides could be encapsulated within pH sensitive liposomes, without affecting either the encapsulation efficiency nor the size of the vesicles when compared to liposomes containing the plasmid alone (Legendre, J. Y., and Szoka, F. C., Pharm Res. 9:1235 (1992)). In a series of experiments, the WTcys MPB-bA significantly enhanced (P<0.025) the transfection efficiency about 3-fold over plasmid complexed with the cTcysMPB-bA. These data are shown in Table 3 below.

The nuclear import of the virion particles is induced by specific nuclear transport signals contained in the virion structural proteins (Clever, J., et al. PNAS (USA) 88:7333 (1991)).

TABLE 3

Transfection using pH-Sensitive Liposomes
Containing Modified Plasmids

Modified Liposome Encapsulated pCLuc4

|  | cTcysMPB-bA | WTcysMPB-bA |
|---|---|---|
| Increase in Transfection[a] | 0.92 ± 0.46 | 2.93 ± 1.76 |

[a]Transfection efficiency was measured on CV-1 cells in culture (Legendre and Szoka, supra).
The CV-1 cells were transfected in triplicate with 4 μg liposome-encapsulated pCLuc4 free or complexed to WTcysMPB-bA or cTcysMPB-bA at a ratio of 300 peptides/plasmid.
The mean transfection activities obtained with liposomes containing WTcys-pCLuc4 or cTys-pCLuc4 complexes were divided by that of liposomes containing pCLuc4
The ratios obtained from 4 different experiments were averaged (fold increase in Table) and compared using a Student's test [Ho rejected; p ≤ 0.025].
There were no significant differences in liposome diameter or encapsulation efficiencies of the various plasmids used in the above transfection experiments.

This enhancement is similar to that observed when synthetic nuclear proteins are combined with DNA and delivered with reconstituted virosomes (Kaneda, Y., et al., supra).

Example 22
Results and Discussion

In conclusion, the sulfhydryl reactive bis-acridine provides an excellent reagent for the non-covalent attachment of sulfhydryl containing molecules to ds DNA. By employing a combination of different effector peptides that mimic the attributes of various biological viruses, superior novel synthetic gene delivery complexes have been unexpectedly produced.

Example 23
Delivery of Oligonucleotides into Cells in Culture by Dendrimers 1.2 μg fluorescein-labeled oligonucleotides in 330 μl Hepes Buffer Saline (HBS:10 mM Hepes, 150 mM NaCl pH 7.4) were placed in a polystyrene tube and 170 μl of HBS containing 100 μg of a sixth generation polyamidoamine dendrimer (SD68) were added dropwise with very slight mixing. After 30 minutes at room temperature, 1.5 ml of serum-free DME H21 medium was added, and the mixture applied to cells in culture. Typically, 100 μl of the complex were added to each 22 mm coverslip containing 80% confluent CV-1 cells plated 24 hrs. earlier. After 2 to 4 hrs., the coverslips were washed with DME H21-10% FCS and mounted unfixed on depression slides. These slides can accommodate 200 μl of medium below the coverslip and were sealed at the edges with warm paraffin.

For analysis, the coverslips were visualized by Laser Scanning Confocal Microscopy. A BioRad MRC-600 confocal system employing a Krypton-Argon laser (excitation: 488 nm, and Nikon inverted microscope were employed. A typical setting for analysis utilized for the tests was as follows.

High Laser Setting
Neutral Density=1
Gain=7
Aperture=10
Auto Black On
Kalman Averaging=3
Objective=63×

Cells were scored as positive based on the presence of unequivocal nuclear fluorescence and the existence of a visual border between the nucleus and the cytoplasm. The fraction of fluorescent nuclei observed was calculated by counting the number of flourescent nuclei observed and dividing by the total number of cells in random healthy fields.

Example 24
Dendrimer to Oligonucleotide Ratio for Nuclear Accumulation of Oligonucleotides The effect of the SD68 dendrimer polycation utilized in Example 23 mediating nuclear accumulation of oligonucleotide in a dose-dependent manner is shown in FIG. 7. Varying amounts of dendrimer polycation (3–200 μg/prep) were prepared as described above with a fixed amount of oligonucleotide (1.2 μg/prep). These were added to the CV-1 cells as per standard procedures and assayed for nuclear fluorescence. It was observed that a threshold ratio of dendrimer polycation to oligonucleotide was required for nuclear accumulation. Beyond this, nuclear staining was observed up to about 25%. Table 4 below shows the charge and oliginucleotide to dendrimer ratios for each test, and the resulting nuclear accumulation of fluorescence (nucleotide).

TABLE 4

Conditions and Results

| Dendrimer (μg) | Oligo (μg) | Pos:Neg Ratio | Oligos/Dendrimer | % Nuclear Positives |
|---|---|---|---|---|
| 3.125 | 1.2 μg/prep | 3.5 | 55.5 | 0% |
| 6.25 | " | 7.0 | 27.0 | 0% |
| 12.5 | " | 14.0 | 13.5 | <0.5% |
| 25 | " | 27.9 | 6.6 | 2% |
| 50 | " | 55.8 | 3.3 | 14% |
| 100 | " | 111.6 | 1.6 | 25% |
| 200 | " | 223.3 | .85 | 20% |

Example 25
Time Dependence of Dendrimer-Mediated Nuclear Accumulation of Oligonucleotide The time dependence with which the SD68 dendrimer polycation facilitated the nuclear accumulation of the oligonucleotides is shown in FIG. 8. A standard preparation of dendrimer polycation-oligonucleotide was added to CV-1 cells which were washed, mounted, and visualized at 5, 30, 60, 90, 120 and 180 minutes. Cells were scored as positive or negative based on the presence or absence of nuclear fluorescence as described above. Nuclear accumulation was seen as early as 30 min after the time of contact and reached nearly 80% in 3 hrs.

Example 26
Effect of Dendrimer Size on Ability to Mediate Nuclear Accumulation

The generation of the dendrimer, corresponding to size, affects its ability to facilitate nuclear accumulation of oligonucleotides. Standard preparations of dendrimer-oligonucleotide were prepared with varying sizes of dendrimer (SD22, SD68, SD124). Each was applied to CV-1 cells for 4 hrs. and assayed for nuclear accumulation as usual. The experiment was performed in DME H21 or an optimized media of reduced ionic strength. SD68 could mediate nearly 80% nuclear accumulation While SD22 and SD124 were somewhat less efficient as mediators of nuclear accumulation under reduced ionic conditions. The results of this test are shown in FIG. 9.

Example 27
Reduced Ionic Strength Increases Nuclear Accumulation of Oligonucleotide The dendrimer polycation-oligonucleotide complexes were prepared as described above. These were diluted with either DME H21 or DME H21 diluted 30% with an equiosmolar, non-ionic solution of a saccharide including glucose, lactose, mannitol, sorbitol and sucrose. The complexes were applied to CV-1 cells for 2 hrs. and analyzed as described above. Regardless of the type of carbohydrate used, reduced ionic strength augmented the dendrimer-mediated nuclear accumulation. The conditions and results of the test are shown in FIG. 10.

Example 28
Attachment of Targeting Ligands and Membrane Destabilizers to DNA via bis-acridines and Combination with the Dendrimer The peptide GALA cys was attached to the bis-acridine maleimide as described in Example 21 to prepare a DNA associating membrane destabilizer. The amino acid cysteine was attached to the bis-acridine maleimide as described in Example 21 as a control. Six microgranis plasmid containing the luciferase gene were diluted 330 µl into HBS in a polystyrene tube. GALA cysMPB-bis-acridine (1 nmol) or cysMPB-bis-acridine and/or 6th generation SD68 PAMAM dendrimer (4 µg) were diluted in 170 µl HBS and added dropwise to the DNA. The tube was gently mixed and after 20 min the resulting complexes were tested for transfection on freshly isolated hepatocytes.

In a similar fashion the (galactose-6)3Lys2bis-acridine (Haensler, J. and Szoka, F., Bioconjugate Chemistry 4:85 (1993)) was attached to DNA and a complex formed with the SD68 dendrimer.

In addition, both the GALA cysMPB-bis-acridine and the (galactose-6)3Lys2bis-acridine were mixed at 0.5 nmol each and added to DNA along with the dendrimer. The composition containing the three components was then added to the hepatocytes as described above. The results are presented in FIG. 11. The amounts of components in each transfection are given beneath the luciferase activity. Adding either the membrane destabilizer GALA cysMPB-bis-acridine or the targeting ligand (galactose-6)3Lys2bis-acridine to the dendrimer increases transfection by at least two orders of magnitude. Adding the two effectors together to the dendrimer but at a reduced quantity also was able to increase transfection. However, adding the control cysMPB-bA to the dendrimer did not increase transfection.

Example 29
Attachment of Targeting Ligand and Membrane Destabilizer Directly to Dendrimer and Mixing in Various Proportions to Increase Transfection Thio-galactose was attached to the SPDP-modified dendrimer 40 Å in diameter (SD40) as described in Example 4 and mixed with unmodified SD40 dendrimer and GALA cys dendrimer. The mixtures of the dendrimers were used to transfect hepatocytes with the luciferase plasmid. The results are given in FIG. 12. The highest levels of transfection were observed when the dendrimer/gal-dendrimer/GALAGALAcys/SEQ ID NO:8-dendrimer ratio was 24/141/42 on a weight basis.

The invention now being fully described, it will be apparent to one of ordinary skill in the art that many changes and modifications can be made thereto without departing from the spirit or scope of the invention as set forth herein.

What is claimed is:

1. A composition for presenting a polynucleotide to a eukaryotic cell, comprising
   a polynucleotide; and
   a dendrimer polycation having terminal cationic groups non-covalently coupled to the polynucleotide;
   wherein the proportion of terminal cationic groups of the dendrimer polycation to nucleotide content of the polynucleotide is 1:1 to 223.3:1.

2. The composition of claim 1, wherein the dendrimer polycation comprises a core molecule comprising at least two reactive residues selected from the group consisting of hydroxyl, ester, imino, imido, halide, carboxyl, carboxyhalide, maleimide, dithiopyridyl and sulfhydryl, and combinations thereof.

3. The composition of claim 1, wherein the dendrimer polycation comprises a polyamidoamine.

4. The composition of claim 1, wherein the terminal cationic groups are selected from the group consisting of azoles and primary, secondary, tertiary and quaternary aliphatic, and aromatic amines which may be substituted with S or O, guanidium and combinations thereof.

5. The composition of claim 1, wherein the terminal cationic groups comprise about 10 to 100% of all terminal groups of the dendrimer polycation.

6. The composition of clainm 5, wherein the dendrimer polycation further comprises 0 to about 90% terminal reactive residues of all terminal groups of the dendrimer polycation.

7. The composition of claim 6, wherein the terminal reactive residues are selected from the group consisting of ester, halide, carboxyhalide, hydroxyl, cyano, carboxyl, sulfhydryl, maleimide and dithiopyridyl, and combinations thereof.

8. The composition of claim 1, wherein
the dendrimer polycation is non-covalently associated with the polynucleotide.

9. The composition of claim 1, wherein the dendrimer polycation has an about 2,000 to 1,000,000 MWave.

10. The composition of claim 1, wherein the dendrimer polycation has a hydrodynamic radius of about 11 to 60 Å.

11. The composition of claim 1, wherein the proportion of terminal cationic-groups of the dendrimer polycation to nucleotide content of the polynucleotide is about 1:1 to 25:1.

12. The composition of claim 1, further comprising a membrane-permeabilizing agent, wherein the membrane-permeabilizing agent is coupled to the dendrimer polycation.

13. The composition of claim 12, wherein the proportion of the membrane permeabilizing agent to terminal cationic groups of the dendrimer polycation is about 1:100 to 1:4.

14. The composition of claim 12, wherein the membrane-permeabilizing agent comprises an amphipathic peptide.

15. The composition of claim 14 wherein the amphipathic peptide assumes a pH-dependent α-helix conformation.

16. The composition of claim 15 wherein the amphipathic peptide α-helix comprises a first and a second axial face such that the first face is substantially charged and the second face is substantially neutral.

17. The composition of claim 16 wherein the first face is negatively charged.

18. The composition of claim 17, wherein the amphipathic peptide comprises GALA/SEQ ID NO:11.

19. The composition of claim 14, wherein the peptide comprises an amphipathic peptide which assumes a β-pleated sheet conformation.

20. The composition of 19 wherein the β-pleated sheet amphipathic peptide has a first and second face such that the first face is positively charged and the second face is substantially neutral.

21. The composition of claim 20, wherein the peptide comprises a cyclic peptide.

22. The composition of claim 21, wherein the cyclic peptide is selected from the group consisting of gramicidin S and tyrocidines.

23. The composition of claim 22, wherein the cyclic peptide comprises gramicidin S.

24. The composition of claim 12, further comprising a phospholipid.

25. The composition of claim 24, wherein the phospholipid comprises phosphatidylethanolamine.

26. The composition of claim 25, wherein the phosphatidylethanolamine comprises dioleoylphosphatidylethanolamine.

27. The composition of claim 24, wherein the phospholipid is present in the form of liposomes.

28. The composition of claim 12, further comprising an additional polycation.

29. The composition of claim 28, wherein the polycation comprises a polyamine.

30. The composition of claim 29, wherein the polyamine is selected from the group consisting of polylysine, polyarginine, polyornithine, spermine, spermidine, 3,3'-diamino-bispropylamine, iminobis(N,N)-dimethylpropylamine, iminobis(3-aminopropyl)-1,3-propanediamine, and cationic dendrimers.

31. The composition of claim 12, wherein the membrane-permeabilizing agent comprises a cationic bile salt of chemical formula

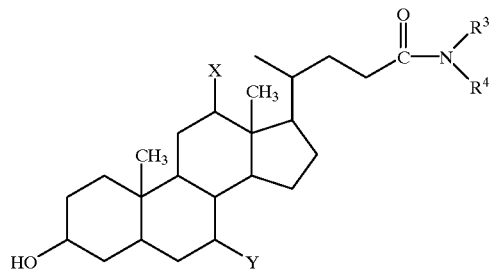

wherein
X and Y are independently H or OH;
$R^3$ is H, $(C_1-C_{10})$alkyl or $(C_1-C_{10})$alkylamine; and
$R^4$ is a positively charged linear or branched $(C_1-C_{30})$ alkyl or $(C_1-C_{30})$alkylamine, wherein one or more of the carbon atoms may be substituted with NR', wherein R' is H, $(C_1-C_{10})$alkyl or $(C_1-C_{10})$alkylamine.

32. The composition of claim 1, further comprising a subcellular-localization agent, wherein the subcellular-localization agent is coupled to the dendrimer polycation.

33. The composition of claim 32, wherein the proportion of the subcellular-localization agent to terminal cationic groups of the dendrimer polycation is about 1:100 to 1:5.

34. The composition of claim 32, wherein the subcellular-localization agent comprises a nuclear localization agent.

35. The composition of claim 34, wherein the nuclear localization agent is coupled to a DNA-associating moiety.

36. The composition of claim 35 wherein the polynucleotide-associating moiety comprises a plurality of linker strands.

37. The composition of claim 36 wherein substantially the entire linker strand sequence is complementary to the desired polynucleotide.

38. The composition of claim 36 wherein the linker strand comprises an extension of the desired polynucleotide.

39. The composition of claim 36 wherein the linker strand has a sequence with a plurality of regions, each region complementary to a portion of the desired polynucleotide.

40. The composition of claim 35 wherein the polynucleotide-associating moiety comprises a first linker complementary to the desired polynucleotide and a second linker complimentary to the desired polynucleotide.

41. The composition of claim 35, wherein the polynucleotide-associating moiety comprises an intercalating agent.

42. The composition of claim 41, wherein the intercalating agent has the chemical formula

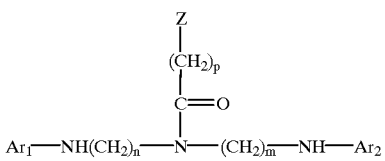

wherein

Z comprises a bond, a reactive group selected from the group consisting of N-hydroxysuccinimide, maleimide, maleimidophenyl, pyridyl disulfide, hydrazide, and phenylglyoxal, or ZY, wherein Y is selected from the groups consisting of cell surface receptor ligands, nuclear localization sequences, and membrane permeabilizing components;

n and m are independently an integer of 1 to 20;

p is an integer of 0 to 20; and $Ar_1$ and $Ar_2$ are independently selected from the groups consisting of ethidium bromide, acridine, mitoxantrone, oxazolopyridocarbazole, ellipticine, N-methyl-2,7-diazapyrenium, and derivatives thereof.

43. The composition of claim 42, wherein $Ar_1$ and $Ar_2$ comprise acridine.

44. The composition of claim 43, wherein Z comprises maleimidophenyl or dithiopyridyl.

45. The composition of claim 42, wherein Z comprises the group

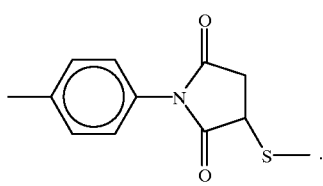

46. The composition of claim 41, wherein the intercalating agent is coupled to at least one ligand comprising a cell recognition agent.

47. The composition of claim 46, further comprising a membrane-permeabilizing agent coupled to the intercalating agent or the ligand.

48. The composition of claim 41, wherein the intercalating agent has the chemical formula

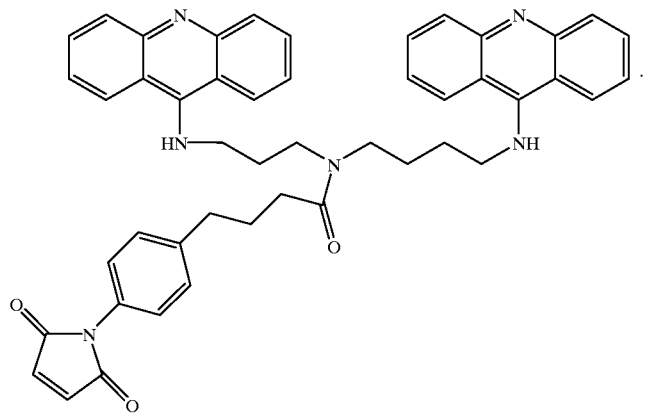

49. The composition of claim 35, wherein the polynucleotide-associating moiety comprises a linker strand complimentary to the desired polynucleotide.

50. The composition of claim 35, wherein the polynucleotide-associating moiety comprises a major- or minor-groove binder.

51. The composition of claim 1, further comprising a cell recognition agent coupled to the dendrimer polycation.

52. The composition of claim 51, wherein the proportion of cell recognition agent to terminal cationic groups of the dendrimer polycation is about 1:100 to 1:10.

53. The composition of claim 51, wherein the cell recognition agent is selected from the group consisting of vitamins, carbohydrates, and polypeptides.

54. The composition of claim 53, wherein the polypeptide comprises an antibody or fragment thereof.

55. The composition of claim 51, further comprising a membrane-permeabilizing agent coupled to the cell recognition agent.

56. The composition of claim 1, further comprising a fusogenic polypeptide, wherein the fusogenic polypeptide is coupled to the dendrimer polycation.

57. The composition of claim 56, wherein the proportion of fusogenic polypeptide to terminal cationic groups of the dendrimer polycation is about 1:100 to 1:4.

58. The composition of claim 1, further comprising a DNA masking agent which increases the circulatory half-life of the polynucleotide, wherein the DNA masking agent is coupled to the dendrimer polycation.

59. The composition of claim 58, wherein the proportion of DNA masking agent to terminal cationic groups of the dendrimer polycation is about 1:33 to 1:3.

60. The composition of claim 58, wherein the DNA masking agent is coupled to a DNA-associating moiety.

61. The composition of claim 58, wherein the DNA-masking agent has the chemical formula

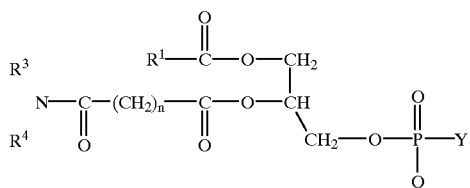

wherein n is an integer of 6 to 24;

Y is selected from the group consisting of hydroxy, sialyl, ethanolamine, choline, glycerol, serine, monomethoxypolyethylene glycol, and inositol;

$R^1$ is $(C_6-C_{24})$alkyl or $(C_6-C_{24})$alkenyl;

$R^3$ is H, or $(C_1-C_{10})$alkyl or $(C_1-C_{10})$alkylamine; and $R^4$ is a positively charged linear or branched $(C_1-C_{30})$ alkyl or alkylamine, wherein one or more of the carbon atoms may be substituted with NR', wherein R' is H, $(C_1-C_{10})$alkyl or $(C_1-C_{10})$alkylamine.

62. The composition of claim 58, wherein the masking agent comprises polyethylene glycol (PEG).

63. The composition of claim 1, wherein the polynucleotide comprises a hybrid vector comprising a structural gene coupled thereto.

64. The composition of claim 1, in solid, liquid or aerosol form.

* * * * *